US008569055B2

(12) United States Patent
Gutova et al.

(10) Patent No.: US 8,569,055 B2
(45) Date of Patent: Oct. 29, 2013

(54) IDENTIFICATION AND CHARACTERIZATION OF CANCER STEM CELLS AND METHODS OF USE

(75) Inventors: Margarita Gutova, La Crescenta, CA (US); Chu-Chih Shih, Arcadia, CA (US); Anna Gevorgyan, San Pedro, CA (US); Karen Aboody, Arcadia, CA (US); Josip Najbauer, Duarte, CA (US)

(73) Assignee: City of Hope, Duarte, CA (US)

( * ) Notice: Subject to any disclaimer, the term of this patent is extended or adjusted under 35 U.S.C. 154(b) by 336 days.

(21) Appl. No.: 12/768,607

(22) Filed: Apr. 27, 2010

(65) Prior Publication Data
US 2011/0003386 A1 Jan. 6, 2011

Related U.S. Application Data

(63) Continuation of application No. 11/693,691, filed on Mar. 29, 2007, now abandoned.

(60) Provisional application No. 60/786,919, filed on Mar. 29, 2006.

(51) Int. Cl.
*C12N 5/09* (2010.01)
*C12N 5/095* (2010.01)

(52) U.S. Cl.
USPC .................... 435/366; 435/325; 435/363

(58) Field of Classification Search
None
See application file for complete search history.

(56) References Cited

U.S. PATENT DOCUMENTS 7,026,282 B1    4/2006   Ploug et al.
2004/0204348 A1 10/2004  Jones et al.

OTHER PUBLICATIONS

Li et al., Cancer Res 2008; 68:1820-25.*
Wang et al., Cell Death Dis 2010; 1, e101; doi:10.1038/cddis.2010.79; published online Nov. 18, 2010.*
Gutova et al., Proc Amer Assoc Cancer Res, Apr. 2006; 47: Abstract #3986.*
Kubo et al., Cancer Sci. 2013; 104:78-84 (pub'd online Nov. 24, 2012).*
Aref, S., et al. 2003. Urokinase plasminogen activator receptor and soluble matrix metalloproteinase-9 in acute myeloid leukemia patients: a possible relation to disease invasion. Hematology 8(6):385-391.
Bachmann, et al. 2005. Recall proliferation potential of memory CD8+ T cells and antiviral protection. J Immunol 175:4677-4685.
Bjerkvig, R., et al. 2005. Opinion: the origin of the cancer stem cell: current controversies and new insights. Nat Rev Cancer 5(11):899-904.
Burgess, et al. 1990. Possible dissociation of the heparin-binding and mitogenic activities of heparin-binding (acidic fibroblast) growth factor-1 from its receptor-binding activities by site directed mutagenesis of a single lysine residue. J Cell Biol 111:2129-2138.
D'Alessio, S., et al. 2004. Antisense oligodeoxynucleotides for urokinaseplasminogen activator receptor have anti-invasive and anti-proliferative effects in vitro and inhibit spontaneous metastases of human melanoma in mice. Int J Cancer 110(1):125-133.
Efferson, et al. 2005. Stimulation of human T cells by an influenza A vector expressing a CTL epitope from the HER-2/neu protooncogene results in higher numbers of antigen-specific TCRhi cells than stimulation with peptide. Anticancer Res 25:715-724.
Foekens, J.A., et al. 2000. The urokinase system of plasminogen activation and prognosis in 2780 breast cancer patients. Cancer Res 60(3):636-643.
Galli, R., et al. 2004. Isolation and characterization of tumorigenic, stem-like neural precursors from human glioblastoma. Cancer Res 64(19):7011-7021.
Hope, K.J., Jin, L., Dick, J.E. 2004. Acute myeloid leukemia originates from a hierarchy of leukemic stem cell classes that differ in self-renewal capacity. Nat Immunol 5(7):738-743.
Kim, C.F., et al. 2005. Identification of bronchioalveolar stem cells in normal lung and lung cancer. Cell 121:823-835.
Kondo, T., Setoguchi, T., Taga, T. 2004. Persistence of a small subpopulation of cancer stem-like cells in the C6 glioma cell line. Proc Natl Acad Sci USA 101(3):781-786.
Lahad, J.P., Mills, G.B., Coombes, K.R. 2005. Stem cell-ness: a "magic marker" for cancer. J Clin Invest 115(6):1463-1467.
Lakka, S.S., et al. 2005. Specific interference of urokinase-type plasminogen activator receptor and matrix metalloproteinase-9 gene expression induced by double-stranded RNA results in decreased invasion, tumor growth, and angiogenesis in gliomas. J Biol Chem 280(23)21882-21892.
Lazar, et al. 1988. Transforming growth factor a: mutation of aspartic acid 47 and leucine 48 results in different biological activities. Mol Cell Biol 8:1247-1252.
Margheri, F., et al. 2005. Effects of blocking urokinase receptor signaling by antisense oligonucleotides in a mouse model of experimental prostate cancer bone metastases. Gene Ther 12(8)702-714.
Meijer-van Gelder, M.E., et al. 2004. Urokinase-type plasminogen activator system in breast cancer: association with tamoxifen therapy in recurrent disease. Cancer Res 64(13):4563-4568.

(Continued)

*Primary Examiner* — Sheela J Huff
*Assistant Examiner* — Jessica H Roark
(74) *Attorney, Agent, or Firm* — Perkins Coie LLP; Patrick D. Morris

(57) ABSTRACT

A subpopulation of cancer stem cells expressing elevated levels of uPAR have been identified among a population of cancer cells. Methods are provided for treating proliferative disorders such as cancer by administering one or more uPAR inhibitors. Methods are likewise provided for predicting the likelihood of recurrence of a cancer, preventing recurrence of a cancer, and identifying the likelihood of a cancer to respond to a particular cancer therapy.

3 Claims, 25 Drawing Sheets

(56) References Cited

OTHER PUBLICATIONS

Patrawala, L., et al. 2006. Highly purified CD44+ prostate cancer cells from xenograft human tumors are enriched in tumorigenic and metastatic progenitor cells. Oncogene 25:1696-1708.
Pulukuri, S.M., et al. 2005. RNA interference-directed knockdown of urokinase plasminogen activator and urokinase plasminogen activator receptor inhibits prostate cancer cell invasion, survival and tumorigenicity in vivo. J Biol Chem 280(43):36529-36540.
Rabbani et al. 2002. Urokinase receptor antibody can reduce tumor volume and detect the presence of occult tumor metastases in vivo. Cancer Res 62:2390-2397.
Rao, J.S., et al. 2005. Inhibition of invasion, angiogenesis, tumor growth, and metastasis by adenovirus-mediated transfer of antisense uPAR and MMP-9 in non-small cell lung cancer cells. Mol Cancer Ther 4(9):1399-1408.
Rigolin, G.M., et al. 2003. Soluble urokinase-type plasminogen activator receptor (suPAR) as an independent factor predicting worse prognosis and extra-bone marrow involvement in multiple myeloma patients. Br J Haematol 120(6):953-959.
Sato, et al. 2002. High-affinity urokinase derived cyclic peptides inhibiting urokinase/urokinase receptor interaction: effects on tumor growth and spread. FEBS Letters 528:212-216.
Selleri, C., et al. 2005. Involvement of the urokinase-type plasminogen activator receptor in hematopoietic stem cell mobilization. Blood 105(5):2198-2205.
Skolnick, et al. 2000. From genes to protein structure and function: novel applications of computational approaches in the genomic era. Trends in Biotech. 18:34-39.
Suzuki, et al. 2003. Bikunin target genes in ovarian cancer cells identified by microarray analysis. J Biol Chem 278:14640-14646.
Werle, B., et al. 2004. Cathepsin B, plasminogenactivator-inhibitor (PAI-1) and plasm inogenactivator-receptor (uPAR) are prognostic factors for patients with non-small cell lung cancer. Anticancer Res 24(6):4147-4161.
Wheeler. 1997. Preventive vaccines for cervical cancer. Salud publica de Mexico. 39:1-9.

\* cited by examiner

IDENTIFICATION AND CHARACTERIZATION OF CANCER STEM CELLS AND METHODS OF USE

RELATED APPLICATIONS

The present application is a continuation of U.S. application Ser. No. 11/693,691, filed Mar. 29, 2007, now abandoned which claims priority to U.S. Provisional Application No. 60/786,919, filed Mar. 29, 2006, the disclosures of which are incorporated by reference herein in their entirety, including drawings.

BACKGROUND

The cancer stem cell hypothesis suggests that neoplastic clones are maintained by a small sub-population of tumor cells with stem cell-like properties, and that these cells are responsible for tumor growth and invasiveness (Al-Hajj 2003; Dick 2003; Galli 2004; Hope 2004; Kondo 2004; Singh 2004; Gao 2005). Recently, the concept of "cancer stem cells" has gained more prominence, with increasing evidence to suggest the presence of a distinct subset of cells within the tumor mass that possess high potential for tumorigenicity and invasiveness (Bjerkvig 2005; Lahad 2005). The term "cancer stem cell" has been described operationally as a cancer cell that has the ability to self-renew by asymmetric cell division. Asymmetric cell division results in a second generation malignant stem cell and a cell that gives rise to the phenotypically diverse tumor cell population (Bjerkvig 2005). Tumor cells that combine the traits of stemness and mobility hold important clues for malignant progression (Brabletz 2005a; Brabletz 2005b). Tumor stem cells also have certain features that are common to normal stem cells, such as longer lifespan, higher proliferative potential and ability to migrate.

The abundance of cancer stem cells may vary within different tumors. Studies of myeloid leukemia, breast cancer, and brain cancers have described the defining characteristics of cancer stem cells (Al-Hajj 2003; Dick 2003; Hope 2004; Singh 2004). Cancer stem cells may be responsible for maintaining the malignant potential of a tumor, and may serve as the underlying cause of tumor recurrence. Current treatment strategies may miss targeting this distinct sub-population, and could explain initial therapeutic response and subsequent recurrence. Therefore, there is a need for methods of identifying and characterizing cancer stem cells, which will allow for the development of treatment methods that reduce or eliminate this critical cell population and thereby increase the effectiveness of various cancer therapies.

SUMMARY

In certain embodiments, methods are provided for treating cancer in a subject by administering a uPAR inhibitor. In certain of these embodiments, one or more anticancer agents are administered in conjunction with the uPAR inhibitor.

In certain embodiments, methods are provided for preventing recurrence of cancer in a subject by administering a uPAR inhibitor. In certain of these embodiments, the cancer is in remission.

In certain embodiments, methods are provided for predicting the likelihood that a particular cancer will recur in a subject by measuring uPAR expression in one or more cancer cells from a subject diagnosed with cancer, wherein elevated uPAR expression in the cancer cells indicates a higher likelihood of recurrence.

In certain embodiments, methods are provided for identifying a subject with cancer who is likely to respond favorably to treatment with a uPAR inhibitor by measuring uPAR expression levels in one or more cancer cells obtained from the subject, wherein elevated uPAR expression in the cancer cells indicates a greater likelihood that the subject will respond favorably to the treatment.

In certain embodiments, methods are provided for treating cancer in a subject by measuring uPAR expression levels in one or more cancer cells from the subject, then administering one or more uPAR inhibitors to the subject if one or more of these cells exhibit elevated uPAR expression.

In certain embodiments, methods are provided for identifying the most invasive subpopulation of cells within a cancer cell population, wherein this invasive subpopulation is identified based on elevated uPAR expression levels.

In certain embodiments, a kit is provided for determining the likelihood that a subject with cancer will respond favorably to treatment with one or more uPAR inhibitors. In certain embodiments, such a kit includes a means for measuring uPAR expression levels in one or more cancer cells from said subject.

In certain embodiments, methods are provided for increasing the sensitivity of a cancer cell to treatment with an anti-cancer agent by inhibiting uPAR expression in the cancer cell. In these embodiments, increasing the sensitivity of the cancer cell to treatment increases the effectiveness of the anticancer agent.

In certain embodiments, methods are provided for obtaining one or more cancer stem cells from a cancer cell population by sorting the cancer cell population based on uPAR expression. In these embodiments, cancer stem cells are those cells from the cancer cell population that exhibit elevated uPAR expression. Cancer stem cells identified and isolated by this method are also provided.

In addition to the exemplary embodiments described above, further embodiments and aspects will become apparent by reference to the drawings and by study of the following descriptions.

DETAILED DESCRIPTION

Figure 1A:
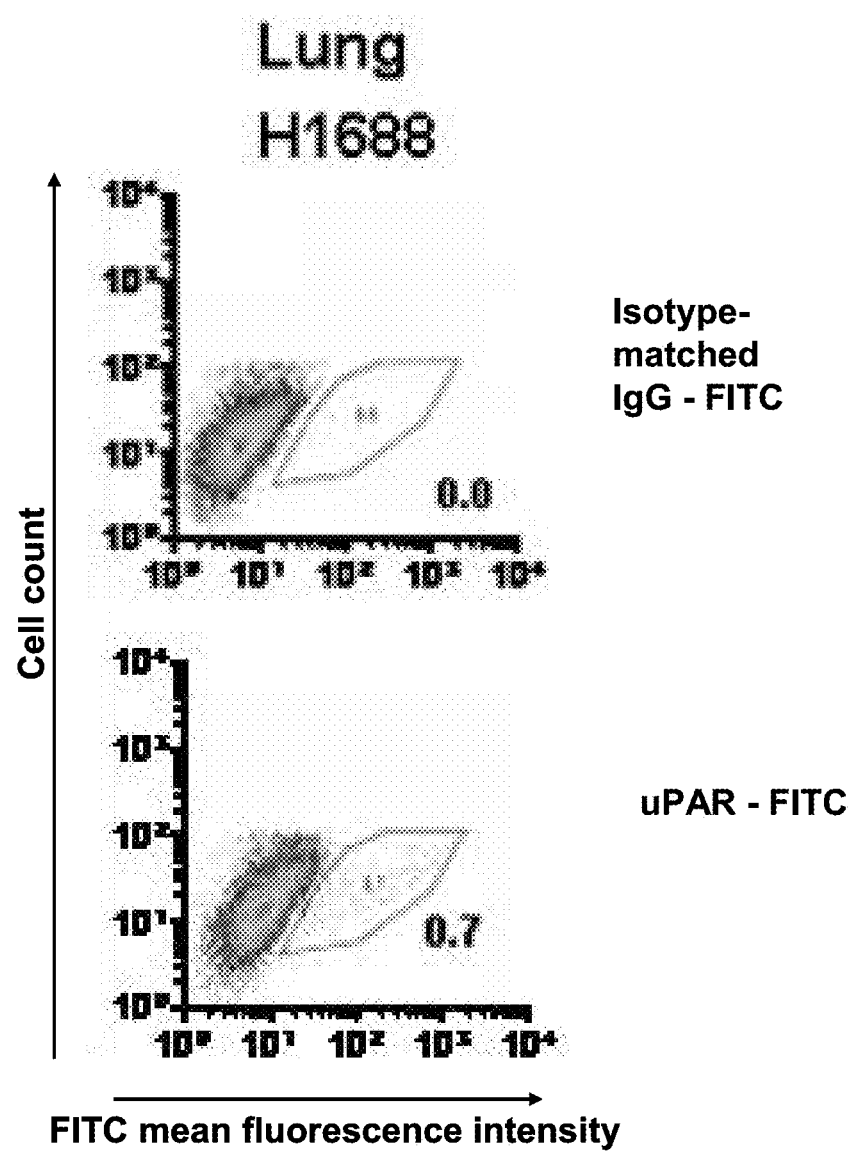
FIG. 1: Flow cytometric analysis of uPAR expression in SCLC-derived cell lines. (A, B, C) Lung-derived SCLC cell lines, (D, E) metastatic bone marrow and (F) metastatic brain cell lines. All cells were cultured in RPMI 1640 medium, stained with uPAR-FITC antibody and analyzed by flow cytometry (lower panels). Control staining was performed using FITC-conjugated, isotype-matched mouse IgG (upper panels). A small population of uPAR-positive cells was detected in all cell lines examined, and is indicated as percent of R1-gated viable cells. Results shown are representative of three independent experiments.
Figure 1B:
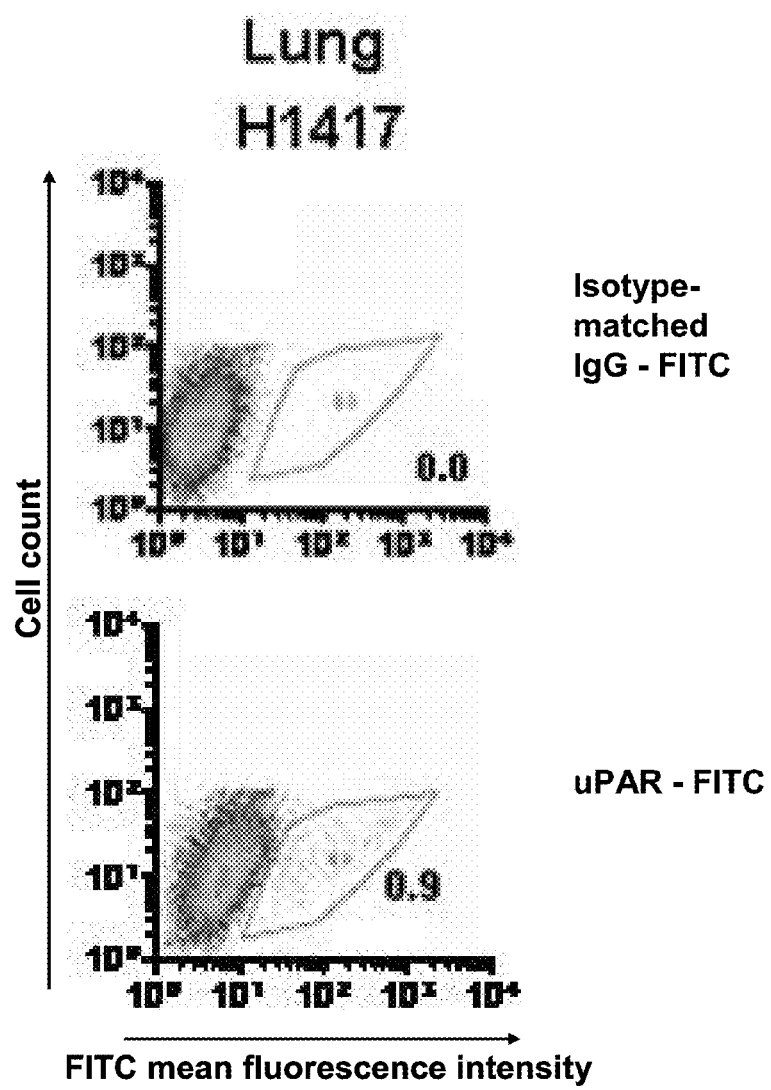
Figure 1C:
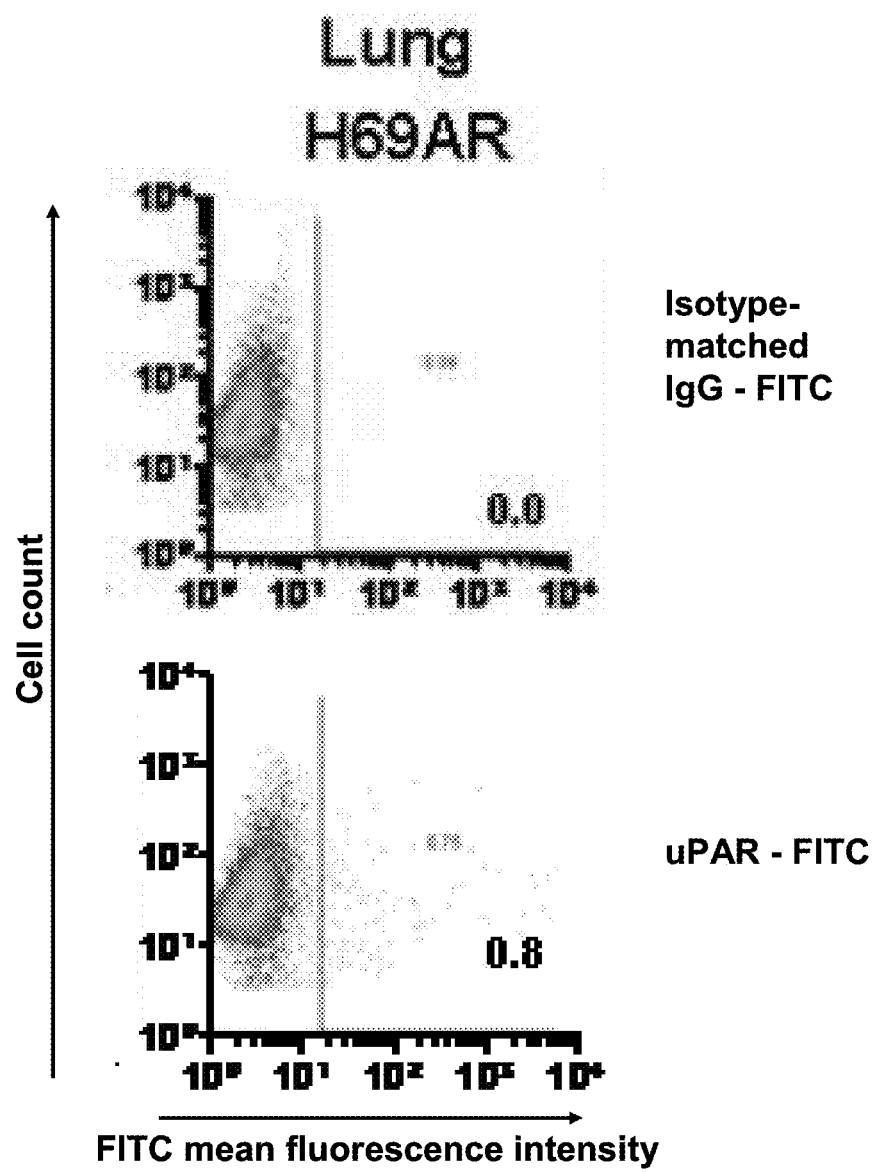
Figure 1D:
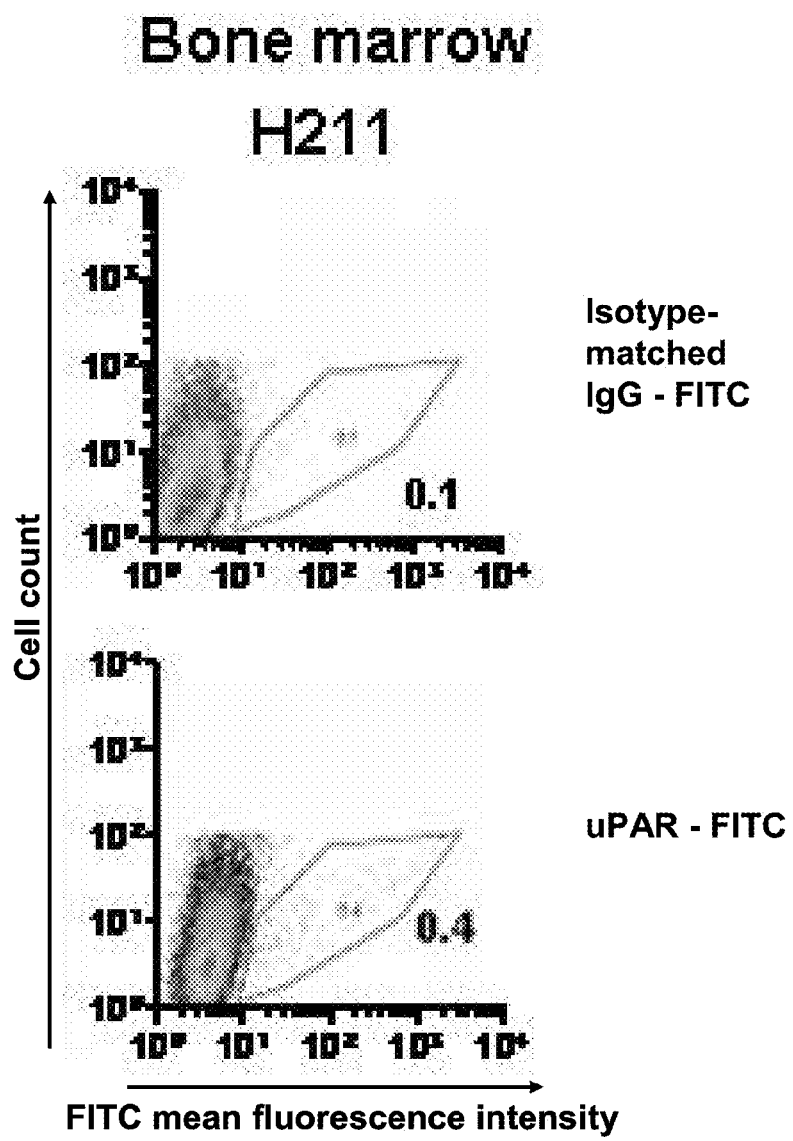
Figure 1E:
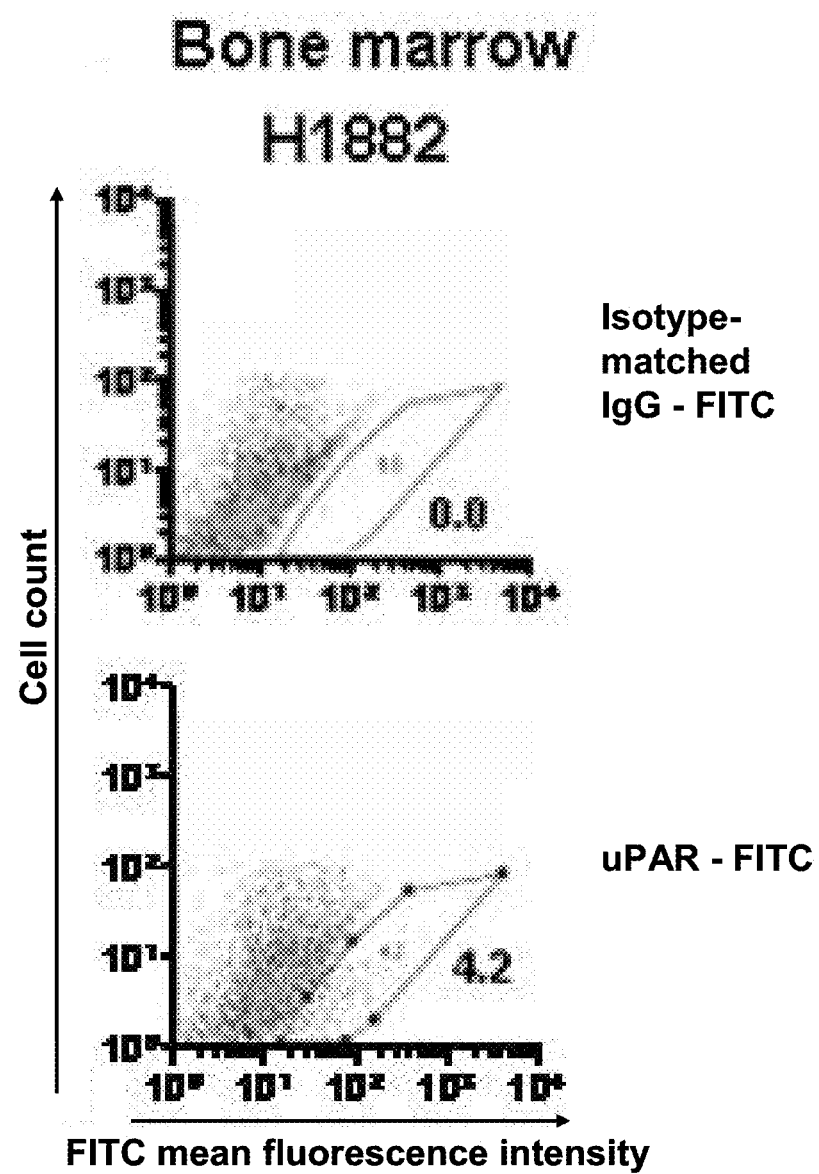
Figure 1F:
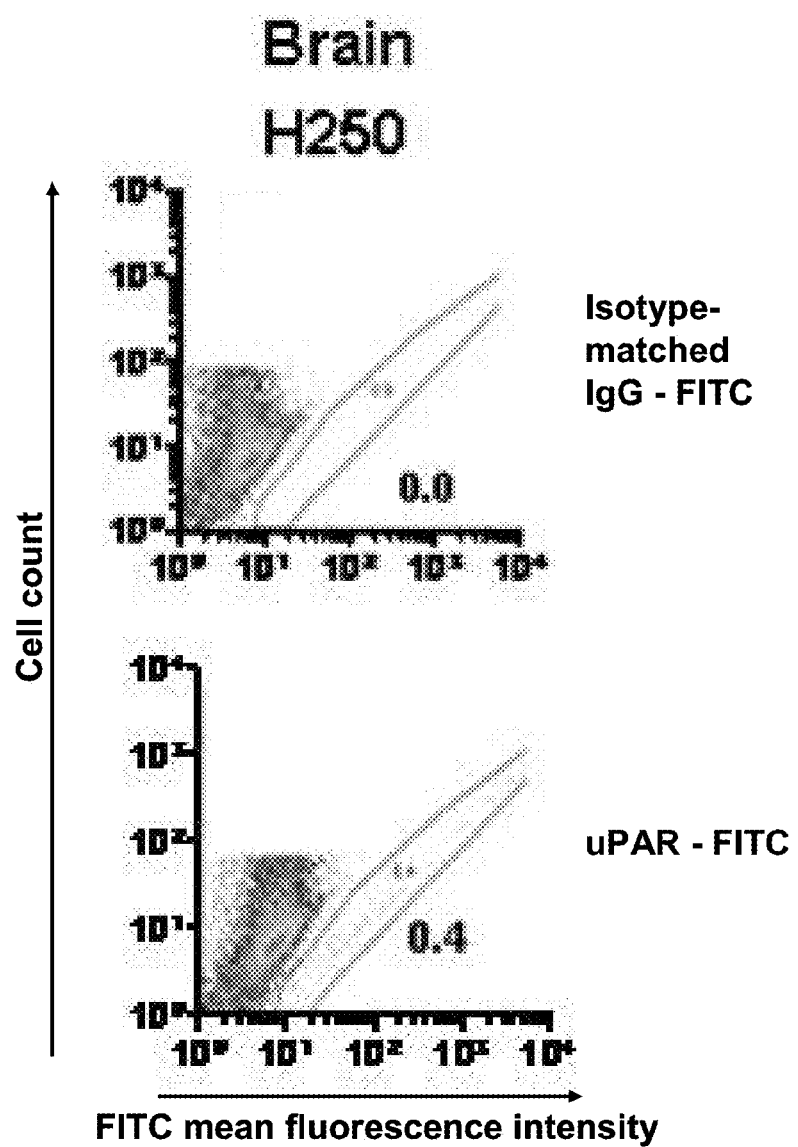

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

ABBREVIATIONS

5-FU, 5-fluorouracil; Bik, bikunin; BM, bone marrow; CM, conditioned media; ECM, extracellular matrix; ELISA, enzyme-linked immunosorbent assay; FACS, fluorescence-activated cell sorting; GFP, green fluorescent protein; HSC, hematopoietic stem cell; MSC, mesenchymal stem cell; NSC, neural stem cell; uPA, urokinase-type plasminogen activator; uPAR, urokinase-type plasminogen activator receptor; SCLC, small cell lung cancer.

DEFINITIONS

The term "uPAR inhibitor" as used herein refers to any agent or treatment method that has the ability to block or reduce uPAR expression or uPAR activity when applied to a cell, and therefore block or reduce activation of the uPA/uPAR system and subsequent intracellular signaling pathways. Examples of uPAR inhibitors include anti-uPAR antibodies, such as for example antagonistic uPAR antibodies, non-antibody uPAR antagonists (competitive and non-competitive), and uPA decoy ligands, as well as agents that inhibit uPAR expression or activity such as uPAR specific siRNA, anti-sense uPAR, and the like.

A uPAR inhibitor "increases the effectiveness" of a cancer therapeutic agent if it increases the ability of the cancer therapeutic to kill or render non-viable a cancer cell or group of cells and/or increases the rate at which the agent is able to kill or render non-viable a cancer cell or group of cells.

RNA interference is a mechanism of post-transcriptional gene silencing in which double-stranded RNA corresponding to a target gene (siRNA) is introduced into a cell, resulting in degradation of the corresponding target mRNA. RNA interference has been shown to be a specific and effective method of inhibiting expression of a specific gene. In one embodiment, a uPAR inhibitor is an siRNA for targeted inhibition of uPAR expression. Gene-specific expression inhibition by double-stranded RNA is generally described in, for example, U.S. Pat. No. 6,506,559, which is incorporated by reference. Exemplary use of siRNA technology in treating human cancer is described in U.S. Patent Application No. 2005/0164970, which is incorporated by reference.

The terms "treat," "treating," or "treatment" as used herein with regards to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

As used herein, "elevated uPAR expression" refers to a level of uPAR expression that is above a specific threshold. In certain embodiments of the invention, this threshold may be that level of expression that has been determined to indicate that a cancer cell is a cancer stem cell. In certain embodiments, a cancer cell from a subject exhibits elevated uPAR expression where it exhibits a higher level of uPAR expression than a healthy, non-cancerous cell from the same subject.

As used herein, the term "reducing the severity" means an arrest or decrease in clinical symptom, physiological indicator or biochemical marker of proliferative disease or cancer. Clinical symptoms include perceptible outward or visible signs of disease. Physiological indicators include detection of the presence or absence of physical and chemical factors associated with a process or function of the body. Biochemical markers include those signs of disease that are observable at the molecular level, such as the presence of a tumor marker. A tumor marker is a substance in the body that usually indicates the presence of cancer. Tumor markers are usually specific to certain types of cancer and are usually found in the blood or other tissue sample. One skilled in the art will be able to recognize specific clinical symptoms, physiological indicators and biochemical markers associated with a particular proliferative disease. For example, for small cell lung carcinoma, neuron specific enolase (NSE), carcinoembryogenic antigen (CEA), lactic dehydrogenase (LDH) and ferritin are biomarkers of SCLC and are used as indicators of extent of disease at diagnoses and monitor of response to therapy.

The terms "migrating cancer stem cells" and "cancer stem cells" as used herein with regards to a sub-population or subtype of tumor cell refers to those cells within a population of tumor or cancer cells possessing stem cell-like properties or phenotypes common to normal stem cells. Such phenotypes or characteristics include, for example, longer lifespan, higher proliferative potential and greater ability to migrate and metastasize.

Cancer Stem Cells

The serine protease urokinase-type plasminogen activator (uPA) and its cell surface receptor (uPAR) play an important role in a number of physiological and pathological processes involved in intravascular homeostasis, extracellular matrix (ECM) integrity, and cell signaling. Binding of uPA to uPAR induces proteolysis-dependent and -independent intracellular signaling, which affects cell adhesion, migration and proliferation in a variety of cells (Blasi 2002).

uPAR is widely expressed on non-malignant and malignant cells, and plays important roles in immune response, tissue regeneration, angiogenesis, cancer growth and metastases (Alfano 2005). uPAR expression results from the activation of several oncogenic pathways including MAPK, RTK, ERK2, FAK (Dick 2003; Singh 2004; Alfano 2005; Almasi 2005). Multiple oncogenic mutations in cancer cells lead to uncontrolled expression of uPA/uPAR (Kondo 2004). Various malignant human tumors, including mammary, lung, bladder, kidney, colorectal, stomach, brain, and ovarian cancers and melanoma overexpress uPAR, and this overexpression is strongly correlated with the most invasive cancer phenotypes and poor survival (Aguirre Ghiso 1999; Foekens 2000; Lakka 2001; Aref 2003; Rigolin 2003; D'Alessio 2004; Meijer-van Gelder 2004; Werle 2004; Almasi 2005; Margheri 2005; Pulukuri 2005). The expression and degradation of uPAR is tightly regulated in normal cells, but the mechanism underlying the overexpression of uPAR in cancer cells remains unknown (Czekay 2001; Blasi 2002; Lee 2003; Alfano 2005; Montuori 2005).

When uPAR was cloned in 1985, it was initially believed that, upon binding to its ligand uPA, the only function of uPAR was the conversion of plasminogen to the serine protease plasmin, which is involved in the degradation of the extracellular matrix (Blasi 2002). However, recent studies have shown that interaction of uPAR with receptors of the integrin family, including G-protein-coupled receptors and vitronectin, leads to activation of several intracellular signal-transduction pathways involved in cell migration, adhesion, proliferation and apoptosis (Aguirre Ghiso 1999; Alfano 2005). As a result of these interactions, uPAR activates intracellular signaling pathways that involve tyrosine and serine protein kinases such as EGF receptor, lymphocyte protein tyrosine kinase (Lck), hematopoietic cell kinase (Hck), Src, focal adhesion kinase (FAK), extracellular signal-regulated kinase (ERK), and mitogen-activated protein kinase (MAPK) (Blasi 2002). Thus, uPAR may be unique among cellular receptors because it plays an instrumental role in both tumor growth and dissemination by stimulation of tumor cell survival and proliferation, and by degradation of ECM to stimulate tumor cell mobility.

Small cell lung cancer (SCLC) is the most aggressive type of lung cancer and has a uniformly poor prognosis (Pisick 2003). Metastases develop quickly, primarily to bone marrow and brain, and are usually present at the time of diagnosis. In untreated patients, median survival is two months from the onset of symptoms (Pisick 2003). Higher mortality in squamous cell and non-small cell lung cancer is correlated with increased levels of uPAR, detected by immunohistochemistry and ELISA (Werle 2004; Almasi 2005). Conversely, inhibition of uPAR in a mouse model of non-small cell lung cancer inhibited tumor growth, invasion, angiogenesis and metastasis (Rao 2005).

As disclosed herein, uPAR expression has been identified as an important marker in a small subpopulation of cells with cancer stem cell phenotypes properties derived from human primary lung small cell lung cancer (SCLC), as well as metastatic bone marrow and brain SCLC. These uPAR-positive cells have a high proliferative potential in vitro, maintain a tumor mass in situ, and form distant metastases in vivo. Additional features of these migrating cancer stem cells include dysfunction of p53 tumor-suppressor protein and higher levels of telomerase activity and activation. The uPAR-positive cancer stem cells identified herein are responsible for primary SCLC tumor growth and formation of distant metastases. Homing of the uPAR-positive SCLC cells to the human brain and bone marrow likely gives rise to micro- and macro-metastatic foci. These uPAR-positive cells persist within the metastases, retaining properties of the primary tumor, potentially giving rise to yet further metastases.

Cancer stem cells should demonstrate characteristics that include: 1) evasion of apoptosis, 2) unlimited replicative ability, 3) potential for tissue remodeling with invasion, and 4) formation of distant metastases. The uPAR-positive SCLC cancer stem cells identified herein appear to fit these criteria, which is consistent with previous experimental evidence supporting the role of uPAR in each of these processes (Lakka 2005; Margheri 2005).

It has been hypothesized that tumor stem cells are responsible for maintaining the malignant potential of a tumor, and may serve as an underlying cause of tumor recurrence (Kim 2005; Patrawala 2006). Current treatment strategies may fail to target the drug-resistant subpopulation, which may explain the initial therapeutic response of the majority of tumor cells followed by later recurrence. Indeed, it was found that uPAR-positive SCLC cells were more resistant to treatment with the cytotoxic agents 5-FU, cisplatin, and etoposide than uPAR-negative cells. Importantly, culturing of SCLC cells in the presence of cisplatin and etoposide resulted in selective killing of uPAR-negative cells, with concomitant enrichment of the uPAR-positive cell population.

uPAR-positive cells isolated from three SCLC lines were able to proliferate and form multiple colonies in methylcellulose media, while uPAR-negative cells displayed little or no clonogenic potential. The clonogenic activity of uPAR-positive cells when compared to uPAR-negative cells demonstrates high proliferative and self-renewal potential in vitro. In addition, uPAR was found to co-express with CD44 and MDR1 in these SCLC cell lines, which may explain the association between advanced malignancy and drug resistance. ATP-binding cassette (ABC) drug transporters have been shown to protect cancer stem cells from chemotherapeutic agents (Dean 2005). A major transporter of the ABC family is P-glycoprotein, the product of the MDR1 gene, which is produced by hematopoietic stem cells (HSGs) (Zhou 2001). The MDR1 gene becomes down-regulated on HSCs upon cell differentiation (Zhou 2001). P-glycoprotein and CD44 have been characterized and are known to be determinants of multi-drug resistance on cancer cells, which is mediated by physical and genetic interactions between CD44 and MDR1 (Miletti-Gonzalez 2005). Activation of CD44 occurs through heterodimerization of CD44 with growth factor receptors (e.g., EGFR, FGFR, HGFR, VEGFR, TGF-bR), which leads to activation of MAP kinase and PI3K-AKT signaling pathways (Kobayashi 2002). CD44 stimulation by its ligand hyaluronan upregulates the expression of uPA and uPAR mRNA, through activation of MAPK-Ras pathway, while PI3K activation stimulates MDR1 expression and function (Kobayashi 2002). PI3K also acts as a positive feedback loop to stimulate hyaluronan production, which activates CD44 (Kamikura 2000; Zoltan-Jones 2003). The CD44-MAPK-PI3K signaling leads to uncontrolled expression of uPA/uPAR and MDR1, which promotes invasive and multi-drug resistant cancer cell phenotype. In addition to the CD44-MAPK-PI3K signaling, uPAR overexpression can induce cell survival by activating the anti-apoptosis factor Bcl-xL transcription (Alfano 2006).

To study the growth and metastasis of the human SCLC lines in vivo, a SCID mouse xenograft model of transplanted normal human lung tissue under the kidney capsule was used to provide a more representative microenvironment for modeling SCLC disease. Using immunohistochemical analysis, uPAR-positive human SCLC cells forming a primary tumor at the xenograft injection site were identified, as well as metastases of uPAR-positive human SCLC cells to the host mouse lung and liver. This indicates that uPAR-positive cells represent a small sub-population of "cancer stem cells" that possess both high proliferative potential and high mobility to establish metastases. Furthermore, injection of unsorted SCLC cell lines that were not specifically enriched for uPAR-positive cells required injection of larger cell numbers in order to establish a tumor, when compared to injection of uPAR-enriched cell population. In addition to providing evidence for the existence of migrating "cancer stem cells" in SCLC, the findings demonstrate that potential cancer stem cells can be isolated from SCLC cell lines. A reliable method for isolation of cancer stem cells using the information provided herein will facilitate the study of the molecular and biological properties of cancer stem cells, and will allow for the identification of more effective cancer therapeutics.

To determine the role of uPAR expression in cancer cell types other than SCLC, uPAR expression was measured in ten cancer cell lines, including lung, brain, colon, breast and prostate cancer cell lines. Of the ten cell lines tested, five (U251, SK-N-AS, MDA-MB-231, PC-3, and CRL-5904) exhibited high levels of uPAR expression.

When uPAR is cleaved at the GPI anchor by endogenous phospholipase D, soluble uPAR (suPAR) is released from the cell membrane. uPA and suPAR levels were measured in conditioned media derived from various cancer cell lines. Activation of uPAR on the tumor cells was found to cause a corresponding increase in uPA and suPAR levels in conditioned media. uPAR expression was also found to induce several cytokines associated with cell migration in conditioned media. For example, IL-8 levels were increased in conditioned media from cancer cells expressing high levels of uPAR. IL-8 was initially characterized for its chemotactic activity towards leukocyte and endothelial cells (Brat 2005). Additionally, IL-8 possesses tumorigenic and pro-inflammatory activity in various high-grade tumors, including gliomas. IL-8 is a downstream target of β-catenin (Levy 2002), and stimulates MMP2 and MMP9 expression in solid tumors (Li 2003).

Human neural and mesenchymal stem cells have been identified for cell based strategies for regeneration of various tissues as well as delivery vehicles for therapeutic agents to target tumors. However, the signals required for homing and recruitment of stem cells to sites of injury and tumors are not well understood. There are several factors in the tumor microenvironment that may contribute to the recruitment of stem cells to tumors. Adhesion molecules such as VLA-4 and P/E selectins, chemokines, their cognate ligands (stromal cell-derived factor 1 (SDF-1) and its receptor CXCR4, and proteolytic enzymes such as elastase and cathepsin G all appear to play a part in facilitating mobilization and homing of hematopoietic stem cells. uPA and uPAR are upregulated in tumors of different origins and play a critical role in the development of the most invasive tumor phenotype. Plasma levels of suPAR are increased in metastatic carcinoma where it has been used for monitoring of disease activity. On the other hand, uPA and uPAR are involved in local and chronic inflammatory response during tissue injury.

The results disclosed herein indicate that activation of the uPA/uPAR system facilitates the trafficking of the stem cells of neural and mesenchymal origin. In vitro migration assays showed that both neural stem cells (NSCs) and mesenchymal stem cells (MSCs) exhibited robust migration towards conditioned media derived from the five tumor cell lines that expressed high levels of uPAR. Only a small level of migration was observed towards conditioned medium from the cancer cells expressing low levels of uPAR. The strong correlation between uPAR expression and stem cell migration indicates that activation of the uPA/uPAR system is responsible for recruitment of both neural and mesenchymal stem cells to tumors.

Cancer patients are often treated with a combination of multiple therapeutic agents such as chemotherapeutic agents. For example, SCLC patients are often treated with a combination of cisplatin with etoposide. Breast cancer patients are often treated with a combination of taxane and anthracycline. This use of multiple agents may increase toxicity risk. The results disclosed herein establish that in addition to promoting tumorigenesis and metastasis, uPAR expression also serves as a useful therapeutic indicator for identifying subjects that are likely to respond favorably to treatment with DNA-damaging therapeutic agents or anti-cancer agents such as for example doxorubicin (Dox), cisplatin, or X-ray irradiation.

In certain embodiments, methods are provided for treating a proliferative disorder characterized by increased expression of uPA/uPAR by administering an effective amount of an agent that inhibits the uPA/uPAR pathway. In certain of these embodiments, treatment is accomplished by inhibiting or blocking uPAR activity, for example by inhibiting uPAR expression. In certain embodiments, the proliferative disorder is cancer. In these embodiments, tumor cell proliferation and/or migration may be inhibited by blocking uPAR activity. Exemplary cancers that can be treated include solid as well as systemic or circulating tumors. For example, hematopoietic neoplasms, leukemia, lymphoma, multiple myeloma, breast, colon, lung, head and neck, liver and biliary tract, pancreatic, kidney, eye, heart, nervous system, urinary tract, genital tract, gastrointestinal tract, endocrine, skin, bones, joints, soft tissue cancers and the like. In certain of these embodiments, one or more uPAR inhibitors may be administered in conjunction with a cancer therapeutic agent, such as for example Dox, 5-FU, carboplatin, cisplatin, etoposide, clophosphamide, vincristine, ifosfamide, topotecan, paclitaxel, methotrexate, vinorelbine, gemcitabine, irinotecan and docetaxel, or X-ray irradiation, either alone or in various combinations. In these embodiments, administration of the uPAR inhibitor(s) may increase the effectiveness of cancer therapeutic agent.

In certain embodiments, methods are provided for reducing cancer recurrence. The method involves administering to an individual in cancer remission an effective amount of one or more uPAR inhibitors, wherein the uPAR inhibitor reduces cancer cell proliferation and/or migration. In certain embodiments, the individual to be treated is in remission from a cancer selected from leukemia, myeloma, breast, lung, colon, melanoma, ovarian, prostate, glioblastoma, and neuroblastoma. The method also includes administering to an individual in cancer remission an effective amount of a uPAR inhibitor and an anti-cancer agent, wherein the combination reduces cancer cell proliferation and/or migration.

An individual in remission from cancer can be treated according to a method of the invention to reduce the risk of cancer recurrence. As used herein, the term "recurrence" means growth or neoplastic or cancerous cells after a tumor or other cancerous condition has been successfully treated such as by surgical or chemically-induced removal or disintegration of cancerous cells. Such recurrence includes dissemination of cancerous cells into local or distant tissues and organs with respect to the location of the primary cancer.

A uPAR inhibitor for use in the methods disclosed herein may be administered by any pathway known in the art that results in the uPAR inhibitor contacting one or more cancer cells. For example, the uPAR inhibitor may be delivered to a subject by oral, topical, sublingual, intraocular, intradermal, parenteral, intranasal, intravenous, intramuscular, intraspinal, intracerebral, or subcutaneous routes, or it may be administered systemically in conjunction with a targeting agent that directs the inhibitor to a cancer cell. In certain embodiments, the tumor-targeting ability of genetically modified normal (non-cancer) stem cells can be used to deliver uPAR inhibitors to tumors overexpressing uPAR and allow the elimination of uPAR-positive cancer stem cell population.

Methods for reducing the severity of a proliferative disease or reducing cancer recurrence, uPAR inhibitor can be formulated with a pharmaceutically acceptable carrier. Suitable pharmaceutically acceptable carriers are known in the art and include, for example, aqueous or organic solvents such as physiologically buffered saline, glycols, glycerol, oils or injectable organic esters. A pharmaceutically acceptable carrier can also contain a physiologically acceptable agent that acts, for example, to stabilize or increase solubility of a pharmaceutical composition. Such a physiologically acceptable agent can be, for example, a carbohydrate such as glucose, sucrose or dextrans; an antioxidant such as ascorbic acid or glutathione; a chelating agent; a low molecular weight polypeptide; or another stabilizer or excipient. Pharmaceutically acceptable carriers including solvents, stabilizers, solubilizers and preservatives, are well known in the art as described, for example, in Martin, Remington's Pharm. Sci. 15$^{th}$ Ed. (Mack Publ. Col., Easton, 1975). Those skilled in the art understand that the choice of pharmaceutical formulation and the appropriate preparation of the compound will depend on the intended use and mode of administration.

Animal models of specific hyperproliferative diseases can be used to assess the efficacy of particular dosages, formulations or routes of administration of uPAR inhibitory agent. A variety of animal tumor models are known in the art that are predictive of the effects of therapeutic treatment. These models generally include inoculation or implantation of a host animal with heterologous tumor cells followed by simultaneous or subsequent administration of a therapeutic treatment. The efficacy of the treatment is determined by measuring the extent of tumor growth or metastasis. Measurement of clinical or physiological indicators can alternatively or additionally be assessed as an indicator of treatment efficacy. Exemplary animal tumor models can be found described in, for example, Brugge et al., Origins of Human Cancers, Cold Spring Harbor Laboratory Press, Plain View, New York, (1991).

In certain embodiments, methods are provided for identifying subjects with an increased risk or likelihood of cancer recurrence based on uPAR expression. Identification of subjects with cancer cells expressing uPAR allows for more individualized therapeutic approaches, which increases the efficacy of therapy and decreases the likelihood and severity of negative side effects. The feasibility of individualized pharmacotherapy is supported by recent studies showing the success of such approaches (Watters 2003; Ross 2004). Utilization of a pharmacogenetic approach is likely to decrease the number of agents that must be administered to a subject, decreasing the risk of toxicity.

In certain embodiments, methods are provided for determining the likelihood that treatment of cancer will be effective, or for determining the extent of effectiveness of the treatment, by measuring uPAR expression levels in one or more cancer cells. In addition, kits are provided for carrying out this measurement. "uPAR expression levels" may refer to protein or mRNA levels, and may be measured by a variety of means well known in the art. uPAR mRNA levels may be measured using any method known in the art, such as for example Northern blot, ribonuclease protection assay (RPA), or a PCR-based approach using one or more sets of primers specific to uPAR. uPAR polypeptide levels may be measured by any method known in the art, such as for example FACS, ELISA or Western analysis using one or more antibodies specific to uPAR or fragments thereof. Alternatively, the level of "uPAR activity" maybe be measured and used to determine the likelihood of cancer recurrence, or extent of effectiveness of a cancer treatment, by measuring indicators correlative of increased or decreased uPAR activity. Such indicators include, for example, migration/invasion assays, cell matrix degradation assays, protease conversion assays and the like.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Expression of Tumor Cell Surface Determinants in SCLC Cell Lines

In order to identify the most invasive SCLC phenotypes, various SCLC cell lines were tested for surface determinants of tumor cells by flow cytometry. SCLC cell lines tested were NCI-H1688 (ATCC No. CCL-257), NCI-H1417 (CRL-5869), and NCI-H69AR (ATCC No. HTB-119) from primary tumor sites in the lung; NCI-H250 (ATCC No. CRL-5828) and NCI-H1915 (ATCC No. CRL-5904) from metastases to the brain; and NCI-H211 (ATCC No. CRL-5824) and NCI-H1882 (ATCC No. CRL-5903) from metastases to bone marrow.

Cell lines were grown in RPMI 1640 modified medium (ATCC, N: 30-2001) supplemented with 10% Fetal Bovine Serum (FBS) for two weeks, except for CRL-5903, which was cultured in complete HITES medium (D-MEM/F-12, N: 30-2006 supplemented with insulin 5 µg/ml, transferrin 10 µg/ml, sodium selenite 30 nM, hydrocortisone 10 nM, β-estradiol 10 nM, L-glutamine 2 mM, HEPES 10 mM and 5% Fetal Bovine Serum).

Cell lines were screened with a panel of antibodies including uPAR (CD87), CD13, CD29, CD44, CXCR4, CD105, CD109, CD166, and for stem cell markers CD34, CD90, CD133, ABCG2/BCRP1. Antibodies were obtained from the following sources: CD59 (CBL467P), CD109 (CBL585P), and CD62E (CBL180F) from Chemicon; CD87 (3936CJ) from American Diagnostica; CXCR4 (FAB170F) from R&D Systems; CD24 (555427), CD90 (555596), CD38 (347680), CD44 (555478), CD45 (555482), CD13 (555394), CD49b (555498), CD29 (555443), and CD3 (30104x) from BD Pharmingen; ABCG2/BCRP1 (10400) from Stem Cell Technologies; CD133/2 (clone 293C3) and CD133/1 (clone AC133) from MACS; CD34 (347660) from Becton Dickinson; CD105 (326-050) from Alexis; MNF116 (F0859) and Cyt18 (F7212) from DACO; and CD166 (3FT) from RDI.

Cells were detached by trypsinization and resuspended in staining buffer (SB) (HBSS, Irvine Scientific, 9228) supplemented with 2% FBS and 10 mM HEPES at a density of $5 \times 10^6$ cells/ml. Fifty µl ($2.5 \times 10^4$ cells) was added to each well of a 96-well v-shaped plate. All antibodies (FITC- or PE-conjugated) were added in concentrations recommended by the manufacturer. Antibodies to CD133, CD34, CD44, CD87, and MDR1 had been individually titrated. The 96-well plates were placed on ice and cells were stained with antibodies for 30 minutes in the dark. After staining, 150 µl of wash buffer (HBSS, supplemented with 15% FBS and 10 mM HEPES) was added to each well, and the plates were centrifuged at 500×g for 5 minutes at 4° C. The cell pellets were resuspended in SB, supplemented with propidium iodide (PI) (1 µg/ml) to exclude nonviable cells, followed by flow cytometric analysis.

The results of this experiment are summarized in Table 1. SCLC-derived cell lines displayed heterogeneous phenotypes with regard to the surface determinants. All SCLC cell lines tested were positive for CD29 (20-99%), CD44 (8-98%), CD105 (3-34%), CD166 (85-98%), and negative for CD90 and CXCR4. uPAR (CD87) was the only cell surface antigen expressed on a small subpopulation of cells (1-4%) in each of the six SCLC cell lines, when analyzed by FACS using anti-uPAR-FITC antibody (FIG. 1, lower panels).

Control samples stained with isotype-matched IgG-FITC were negative for uPAR expression (FIG. 1, upper panels). The consistent presence of a small uPAR-positive subpopulation of cells in all primary (lung, FIG. 1, lower panels A, B, and C) and metastatic (bone marrow, FIG. 1, lower panels D and E; brain, FIG. 1, lower panel F) SCLC cell lines, in contrast to the other markers which varied in abundance, suggests that uPAR-positive cells may comprise a unique subpopulation in of cancer cells.

Example 2

Chemoresistance of uPAR-Positive Cancer Cells to 5-Fluorouracil

To determine if the uPAR-expressing cell population identified in Example 1 was resistant to chemotherapeutic agents, cytotoxicity assays were performed on three cell lines (NCI-H211, NCI-H69AR, and NCI-H1417) using non-sorted (bulk) as well as sorted uPAR-positive and uPAR-negative cell populations.

Cell lines were grown in RPMI 1640 medium. For immunostaining, $4 \times 10^6$ cells were collected and resuspended in 800 µl of SB, followed by staining with uPAR (CD87)-FITC-conjugated antibody as described in Example 1. uPAR-positive and uPAR-negative cells were sorted by FACS using anti-uPAR-FITC-conjugated monoclonal antibodies, followed by culture on "base" methylcellulose media (Stem Cell Technologies, 04100) for 16 days at 37° C., 5% $CO_2$.

Cells were counted, placed into 96-well plates ($4 \times 10^3$ cells/well, in triplicate), and treated with 5-fluorouracil (5-FU) at a final concentration of 0, 3, 10, 100, or 200 µg/ml. After incubation for 72 hours, both viable and dead cells were counted using the Guava ViaCount assay. Only viable cells were included in data analysis. The Guava ViaCount assay distinguishes between viable and non-viable cells based on the differential permeability of DNA binding dyes in the ViaCount reagent. Fluorescence of the dyes allows quantitative assessment of both viable and non-viable cells in suspension. Data was normalized to 100%, which signified the number of uPAR-positive and uPAR-negative cells without drug added.

Figure 2A:
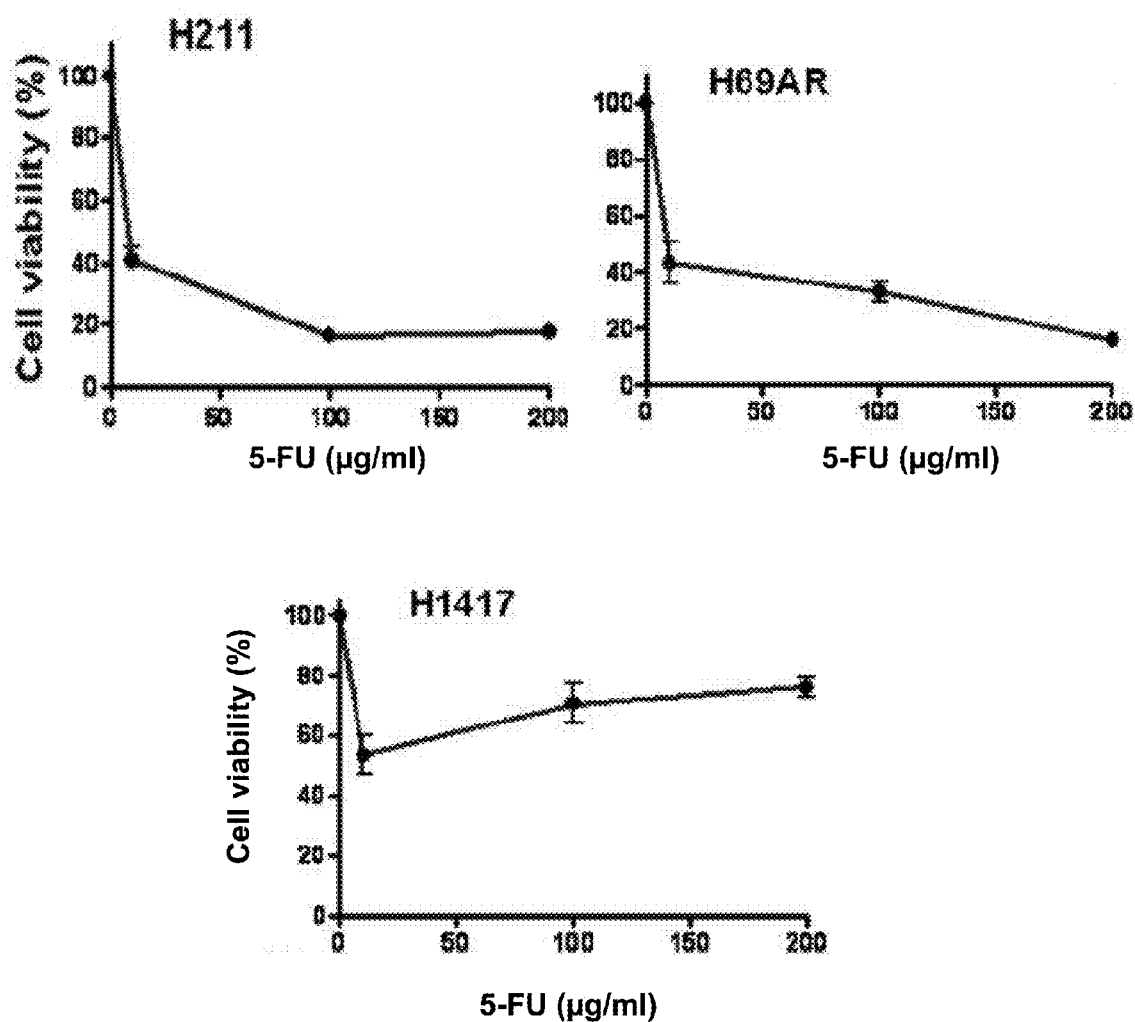
FIG. 2: Cytotoxic effect of 5-FU on non-sorted and sorted (uPAR-positive and uPAR-negative populations) derived from SCLC cell lines. (A) 16104 cells (H211, H69AR, H1417) were placed in wells of a 48-well plate in triplicates and incubated for 72 hr in the presence of varying concentrations of 5-FU. (B) SCLC cell lines were FACS sorted after staining with anti-uPAR antibodies and were plated at the same seeding density (46103/well of 96-well plate) and treated with 5-FU at 0, 10, 100, 200 mg/ml for 72 hr. Cell survival was evaluated after adding Guava ViaCount reagent and counting viable and dead cells. Only viable cells were included in data analysis, and 100% viability was defined as number of viable cells cultured in absence of 5-FU. Statistical analysis (2-way ANOVA) of uPAR(+) and uPAR(2) data sets revealed significant differences among viability of uPAR(+) and uPAR(2) cells (P=0.0002, 0.0027, 0.0008 for H211, H69AR, H1417 cells, respectively). The data points represent averages±SD of three independent experiments.
Figure 2B:
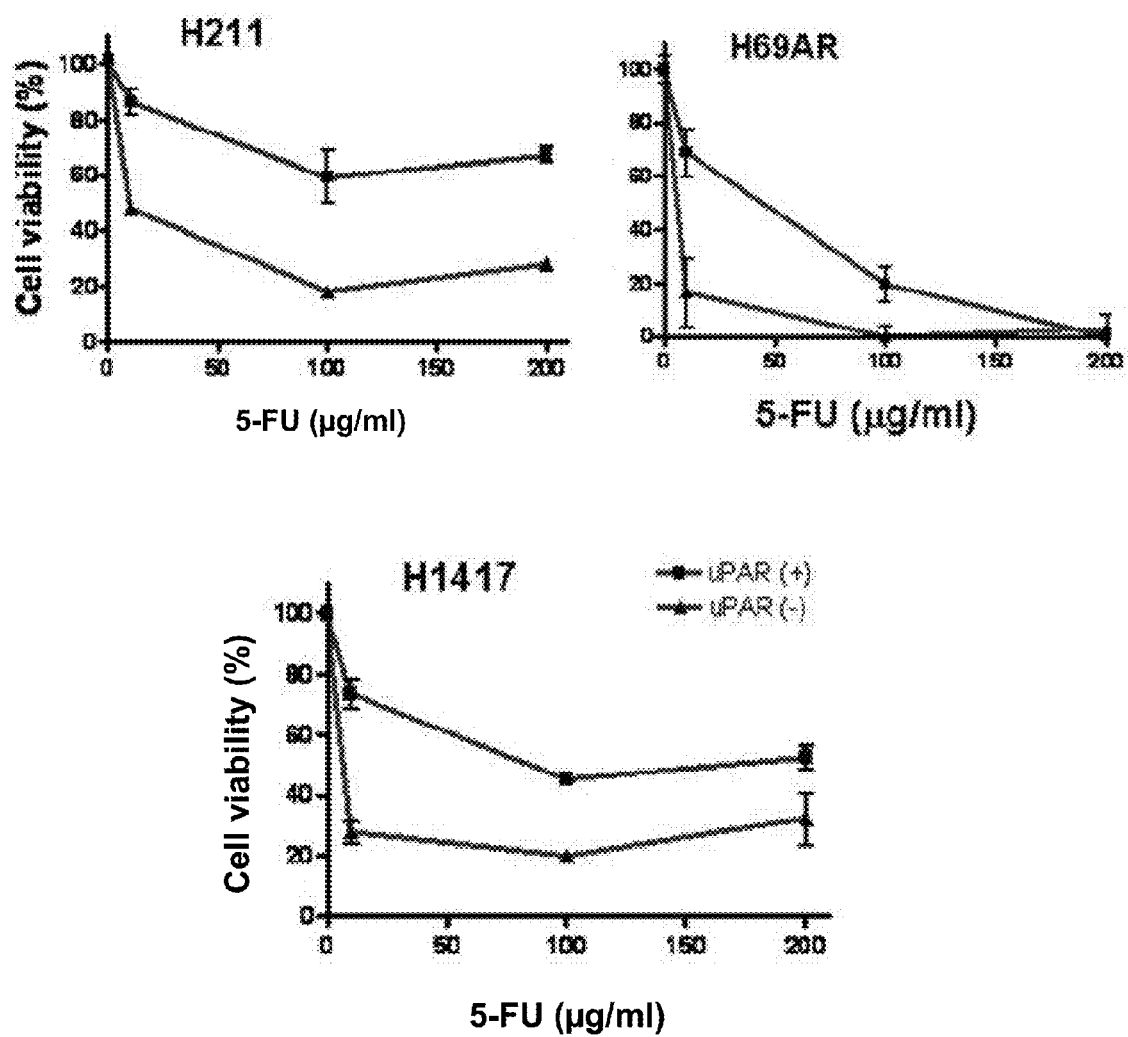

A cell killing effect was detected in all three non-sorted cell lines, where 40-80% of cells were killed by 5-FU (FIG. 2A). Importantly, uPAR-positive sorted cell from the three cell lines displayed significantly increased resistance to 5-FU, with only 40-50% of NCI-H211 and NCI-H1417 cells being killed (FIG. 2B). Although NCI-H69AR cells also showed differential killing of uPAR-positive and uPAR-negative cells (e.g., 10 µg/ml 5-FU killed 30% of uPAR-positive cells, versus 85% of uPAR-negative cells), the killing effect for both populations was the same (approximately 100%) at high (200 µg/ml) 5-FU concentrations.

Example 3

Chemoresistance of uPAR-Positive Cancer Cells to Cisplatin and/or Etoposide

To determine whether the results observed in Example 2 could be generalized to other types of chemotherapeutic agents, a similar experiment was performed using cisplatin and etoposide, two drugs currently used for treatment of patients with SCLC.

Sorted or unsorted NCI-H211, NCI-H69AR, and NCI-H1417 cells were applied to 48-well plates ($1 \times 10^4$ cells/well) and treated with cisplatin, etoposide, or a combination of cisplatin and etoposide at drug concentrations of 0, 3, 10, or 100 µg/ml. The seeding densities per unit area ($mm^2$) were the same in this experiment as in the 5-FU experiment (density=125 cells/$mm^2$). After 72 hours of incubation, viable cells were stained with uPAR-FITC antibodies and evaluated by flow cytometry.

Figure 3A:
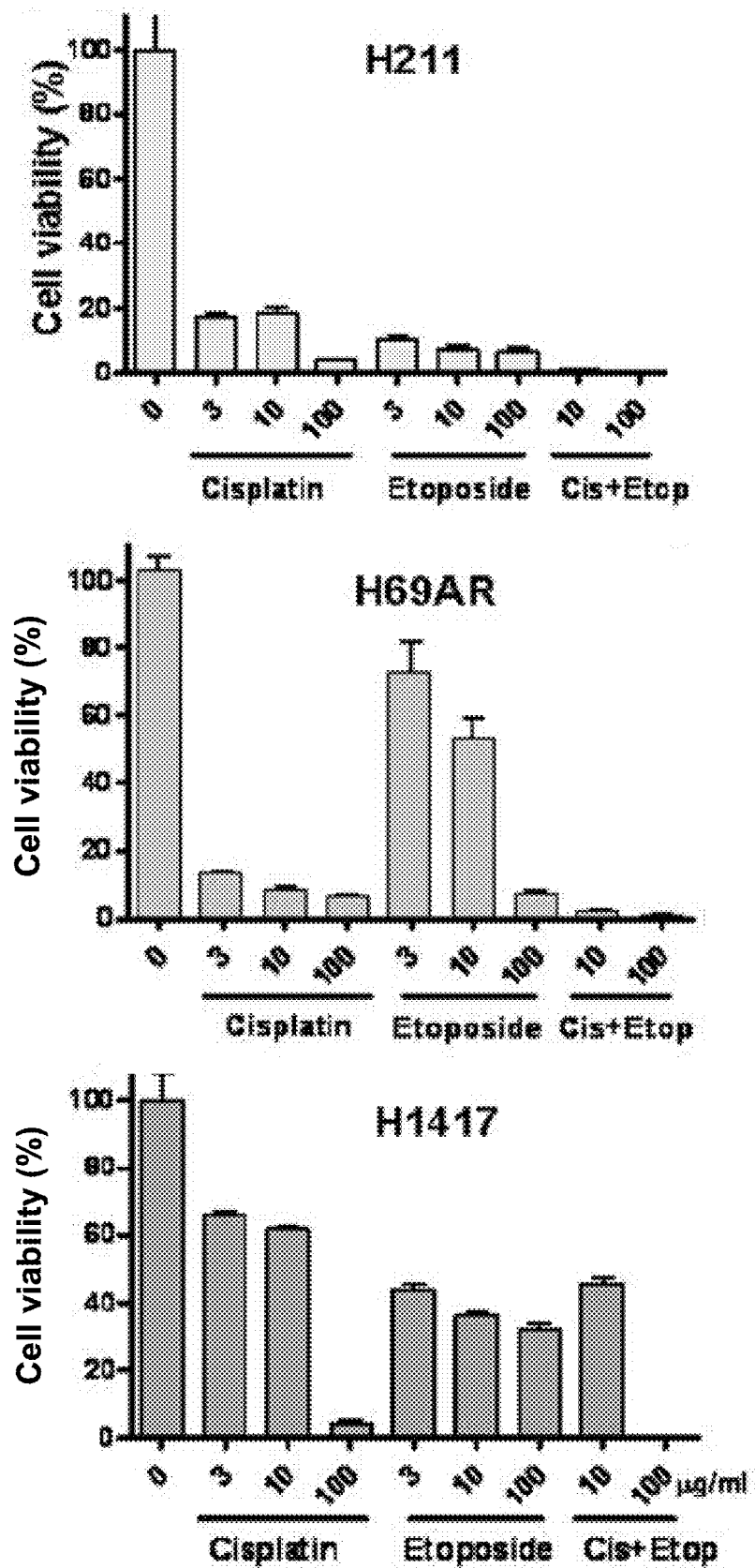
FIG. 3: Cytotoxic effect of cisplatin and etoposide on non-sorted cells derived from SCLC cell lines. (A) SCLC cell lines (non-sorted) treated with cisplatin, etoposide at concentrations 0, 3, 10, 100 mg/ml or their combinations (cisplatin and etoposide at final concentrations of 10 mg/ml, 100 mg/ml) for 72 hr. Cell survival was evaluated after addition of Guava ViaCount reagent and counting of both surviving and dead cells using Guava ViaCount software. Data were normalized as 100% viability of cells cultured in absence of drugs. Error bars indicate standard deviation of triplicate cultures (results of three independent experiments). (B) After treatment cisplatin and etoposide, viable adherent cells were detached by trypsin treatment and were stained with anti-uPAR-FITC antibodies and percentage of uPAR-positive cells was determined by FACS analysis. Sample with mouse IgG isotype control antibody was used to set the value of the FACS gate, which was applied to all samples stained with uPAR-FITC.

60-80% of unsorted cells were killed by cisplatin and etoposide (either separately or in combination) (FIG. 3A). As was seen with 5-FU, the uPAR-positive sorted cells displayed significantly increased resistance to cisplatin and etoposide, with only 30-50% of cells killed versus 60-80% for uPAR-negative sorted cells.

Figure 3B:
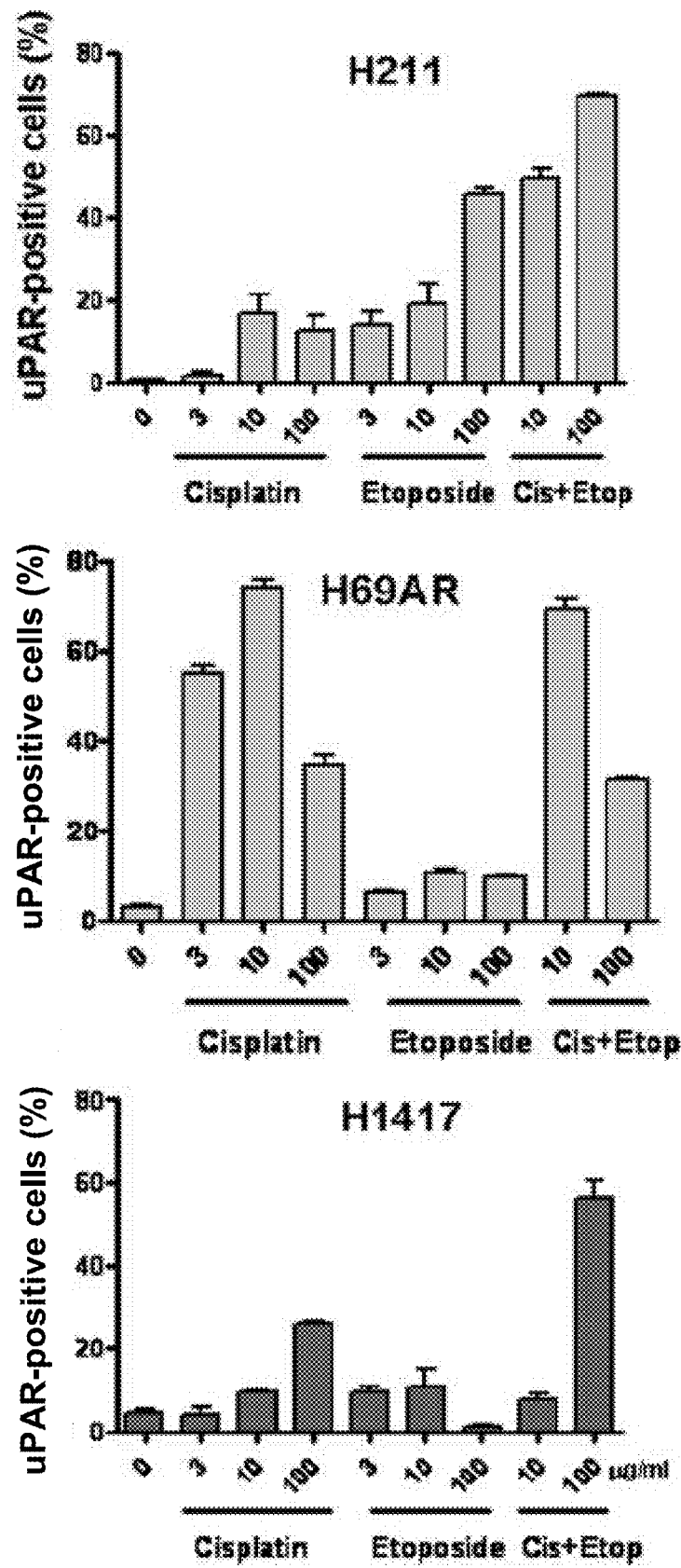

To confirm that uPAR expression confers tumor cell resistance to cisplatin and etoposide, a cytotoxicity assay was performed using the same non-sorted SCLC cell lines, and the cells were examined to see if there was enrichment of uPAR-positive cells in the surviving cell population. A significant enrichment of uPAR-positive cells (40-70%) was observed in the surviving cells, versus only 1-5% of uPAR-positive cells in control cultures grown in the absence of these drugs (FIG. 3B).

The combined results of Examples 2 and 3 establish that uPAR expression confers chemoresistance to SCLC, and that a uPAR-positive cell subpopulation in SCLC is responsible for chemoresistance to chemotherapeutic agents. Therefore, uPAR-positive cells provide a novel target for effective cancer therapy.

Example 4

Clonogenic Activity of uPAR-Positive Tumor Cells

To establish that uPAR-positive cells possess high clonogenic and self-renewal potential, a clonogenic experiment was performed using NCI-H1417 (lung), NCI-H69AR (lung), and NCI-H211 (bone marrow) cells sorted to 97% purity. uPAR-positive and uPAR-negative cells were plated in triplicate in MethoCult medium on a 6-well plate at $3 \times 10^3$, $1 \times 10^3$, or $1 \times 10^2$ cells/ml. Cells were cultured at 37° C., 5% $CO_2$ in a humidified incubator for 16 days. Colonies were counted using an inverted brightfield microscope at 4× magnification.

Figure 4:
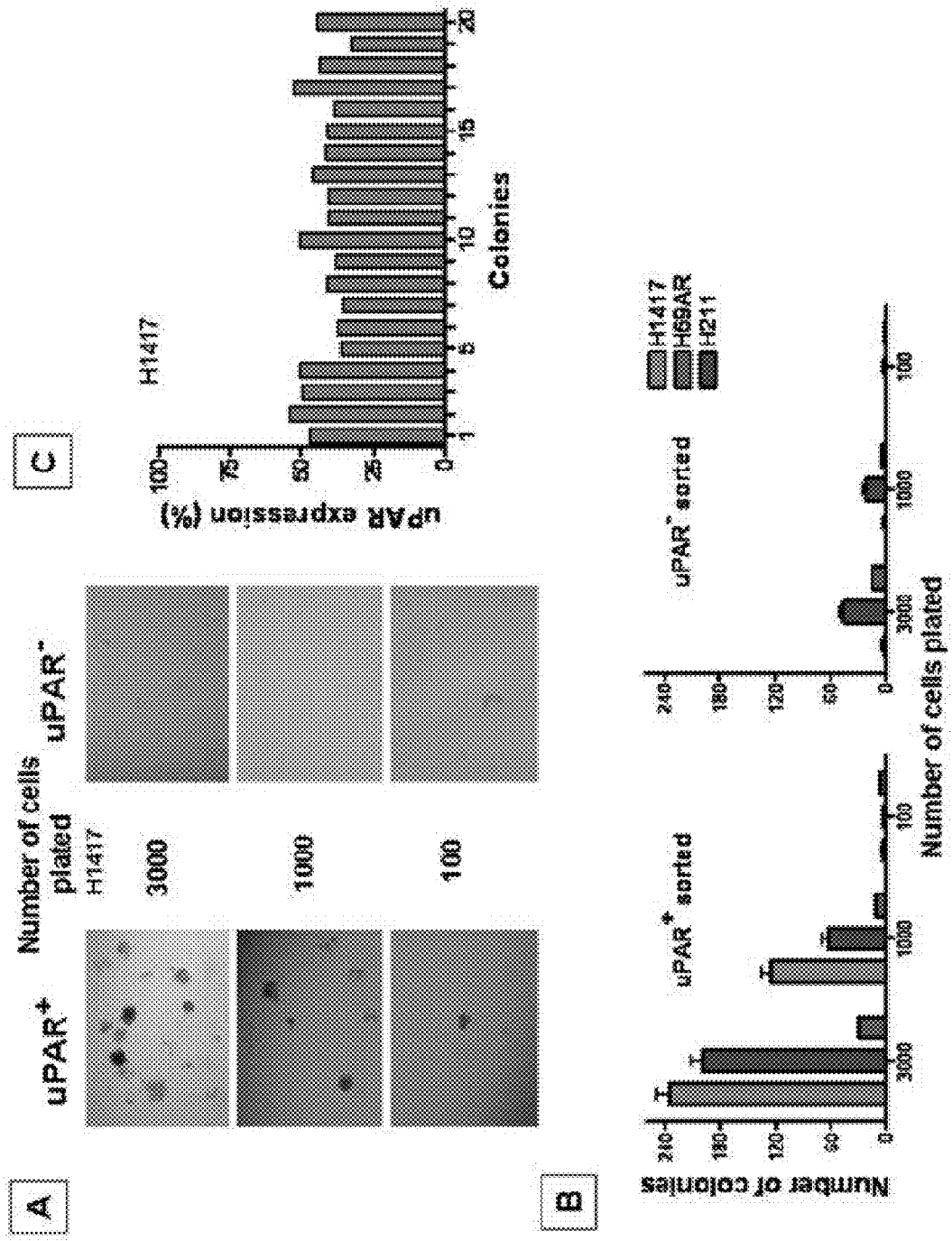
FIG. 4: Colony-forming activity of uPAR-positive and uPAR-negative cells derived from SCLC cell lines. (A) H1417-derived, uPAR-positive sorted cells formed multiple colonies in methylcellulose media, while uPAR-negative cells from the same sorts displayed little or no clonogenic activity. (B) Graphical representation of colony-forming ability of uPAR-positive and uPAR-negative cells at different plating densities 3000, 1000, 100 cells/6-well plate (H1417, H69AR, H211). (C) Distribution of uPAR-positive cells in the colonies derived from sorted uPAR-positive cells grown in methylcellulose media. A total of 20 cell colonies from the H1417 cell line were analyzed.

The uPAR-positive cells formed multiple distinct colonies (FIG. 4A). Approximately 10% of the uPAR-positive NCI-H1417 and NCI-H211 cells formed colonies (FIG. 4B). Conversely, uPAR-negative NCI-H1417 cells did not form colonies, and NCI-H211 and NCI-H69AR cells formed only a few colonies (FIG. 4B).

uPAR-positive and uPAR-negative colonies were isolated and analyzed for uPAR expression by flow cytometry. Both uPAR-positive and uPAR-negative cells were found in every colony derived from sorted uPAR-positive cells. In NCI-H1417 uPAR-positive colonies, 30-50% of cells displayed uPAR positivity after 18 days of incubation (FIG. 4C). In NCI-H211 and NCI-H69AR uPAR-positive colonies, approximately 50% of cells displayed uPAR positivity after 16 days of incubation. This data indicates that uPAR-positive cells can give rise to both uPAR-positive and uPAR-negative cells.

Several uPAR-positive colonies were picked and grown further for two weeks in RPMI culture medium, followed by FACS analysis and a clonogenic assay. A similar proportion of uPAR-positive and uPAR-negative cells (1-5% and 95-99%, respectively) were observed in these cultures, suggesting that uPAR-positive colonies can recapitulate the parental cell phenotype.

Example 5

Co-Expression of uPAR with CD44 and MDR1

Figure 5:
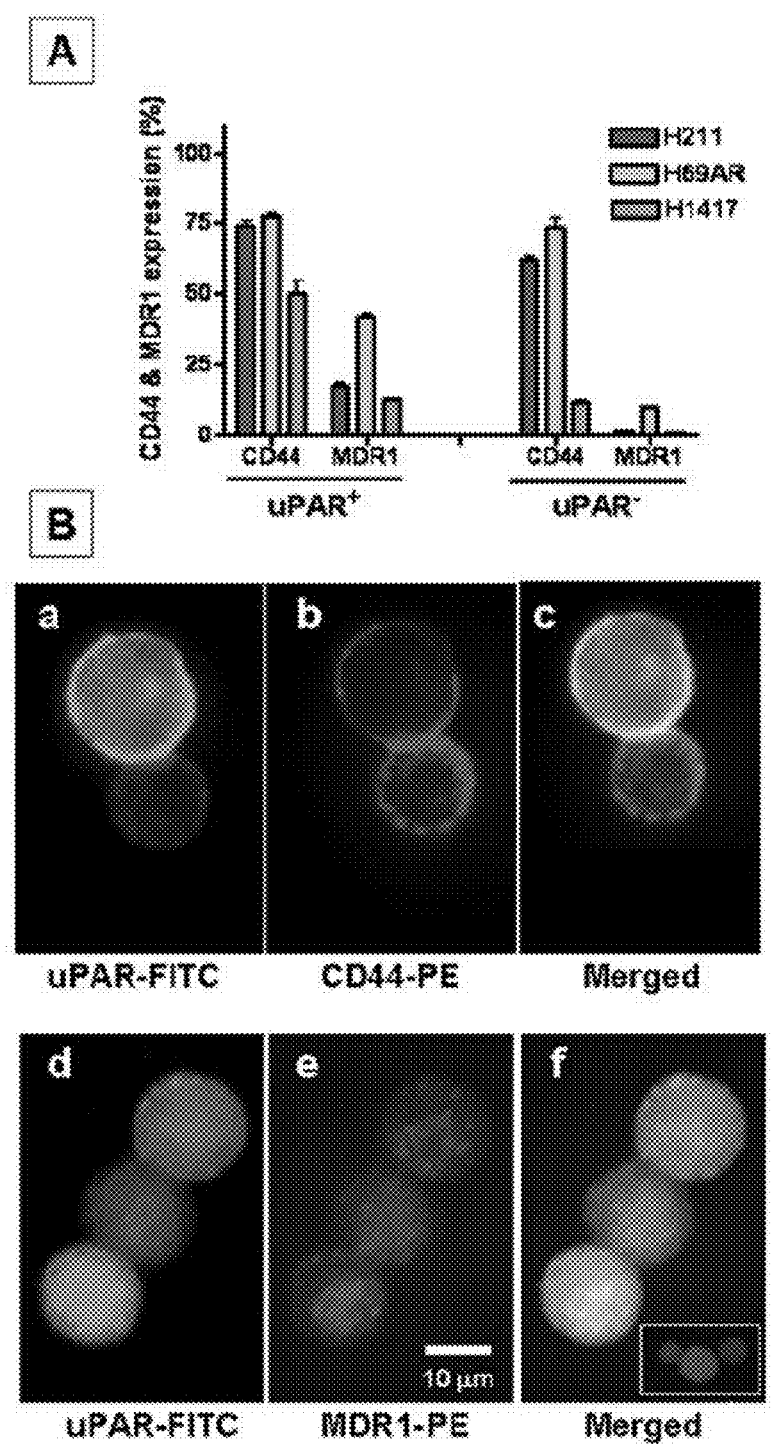
FIG. 5: Expression of CD44 and MDR1 on uPAR-positive and uPAR-negative cells. (A) FACS analysis of, H211, H69AR and H1417 SCLC cell lines double-labeled with uPAR-FITC and CD44-PE, MDR1-PE. The percentages of cells expressing CD44 and MDR1 were calculated separately for uPAR-positive and uPAR-negative cells. (B) Fluorescent microscopic analysis of double-labeled and FACS-sorted cells. Examples of uPAR-FITC/CD44-PE double-labeling (a,b,c) and uPAR-FITC/MDR1-PE double-labeling (d,e,f). (Bf-inset) H1417 cell line stained with mouse IgG isotype control-PE (red), isotype control-FITC (green) and DAPI (blue).

Since uPAR-positive cells appeared to represent a drug-resistant and clonogenic population in SCLC, it was hypothesized that they may express the CD44 and MDR1 (ABCB1) genes, which are involved in the development of cancer stem cell phenotype and multi-drug resistance. To further characterize uPAR-positive cell populations, a double-labeling experiment was performed with uPAR-FITC, CD44-PE, and MDR1-PE on NCI-H211, NCI-H69AR, and NCI-H1417 cells. Cell lines were stained with CD44-PE and MDR1-PE, washed, and then stained with uPAR-FITC ($1 \times 10^5$ cells/1 g of antibody). Iso-type matched PE- or FITC-conjugated antibodies were used as controls. Stained cells were analyzed by flow cytometry.

uPAR-positive cells derived from all three cell lines expressed CD44 on 50-80% of cells and MDR1 on 10-40% of cells (FIG. 5A). Expression of these markers was also confirmed using fluorescent microscropy (FIG. 5B). uPAR-negative cells also expressed CD44 (~70% for NCI-H211 and NCI-H69AR, ~10% for NCI-H1417) and MDR1 (1-10% for all three cell lines) (FIG. 5A). This data suggests an enrichment of CD44 expression on NCI-H1417 cells, and an increase in MDR1 expression in all tested SCLC cell lines.

Figure 6:
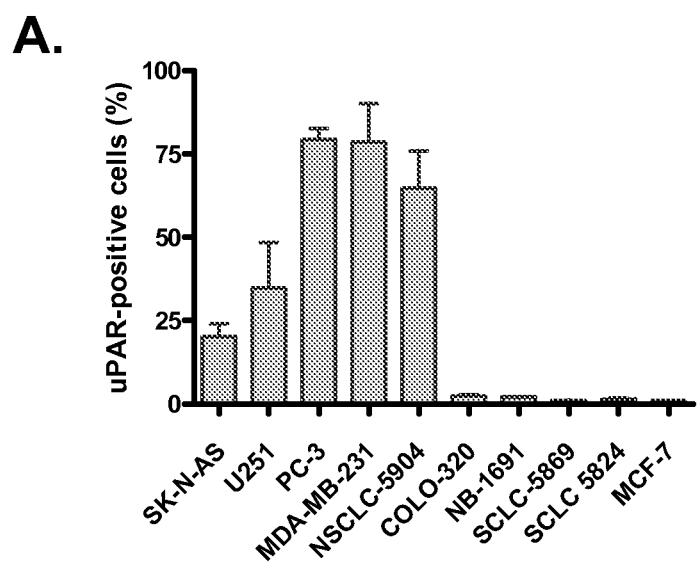
FIG. 6: Expression of uPAR and uPA in various cancer cell types. (A) FACS analysis of uPAR expression. (B) RT-PCR analysis of uPA and uPAR expression. (C) Immunohistochemical analysis of uPAR expression.

Example 6 uPAR Expression in Various Cancer Cell Lines upA and uPAR expression in various cancer cell lines was measured by FACS as described in Example 1. Cell lines tested were SK-N-AS and NB-1691 (neuroblastoma), U251 (glioblastoma), PC-3 (prostate cancer), MDA-MB-231 and MCF-7 (breast cancer), COLO-320 (colon cancer), and the SCLC cell lines NCI-H1915 (ATCC No. CRL-5904), NCI-H211 (ATCC No. CRL-5824), NCI-H1417 (CRL-5869), and NCI-H1688 (ATCC No. CCL-257). uPAR expression data is summarized in FIG. 6A.

Figure 6B:
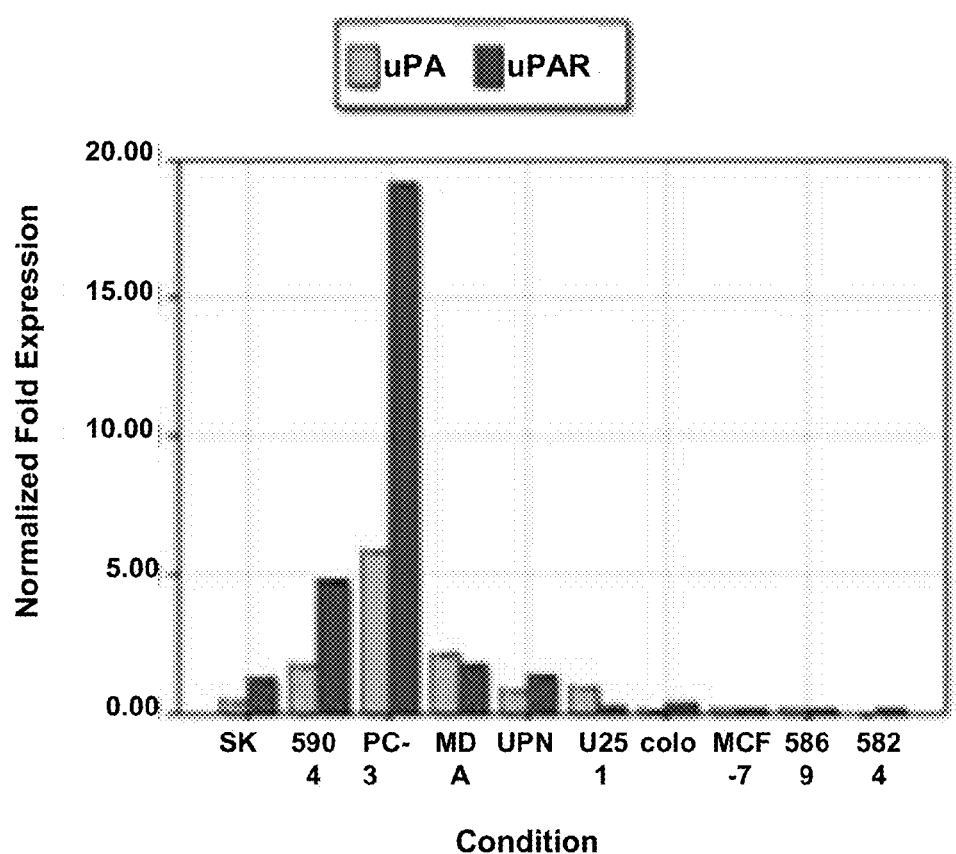
Figure 6C:
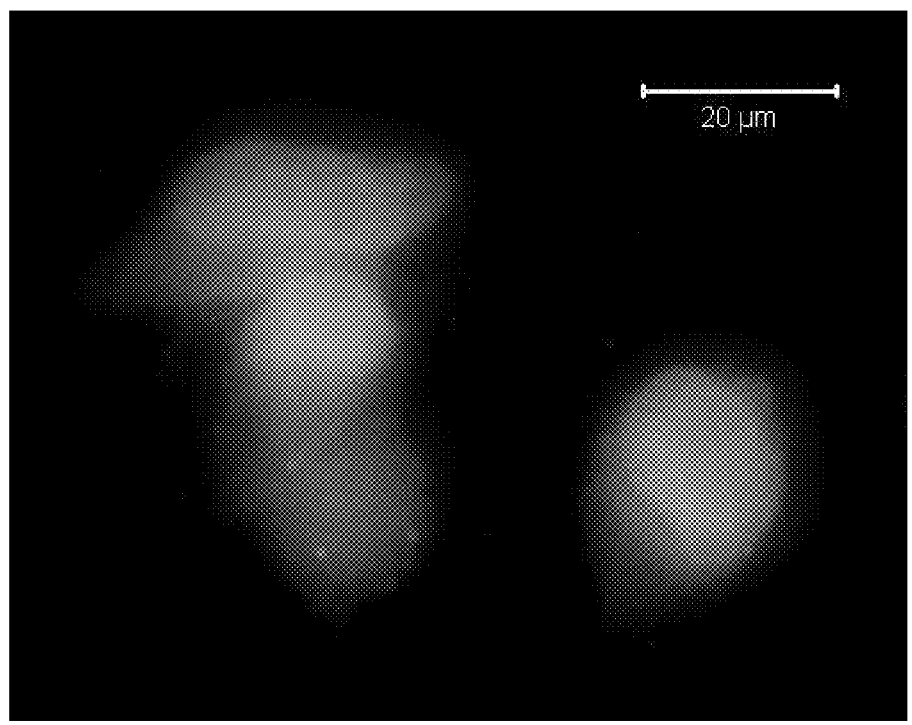

Based on uPAR expression levels, the cell lines were classified as 1) cell lines expressing high levels of uPAR (>20% of cells uPAR-positive) or 2) cell lines expressing low levels of uPAR (<5% of cells uPAR-positive). The cell lines with high uPAR expression were originally derived from the most invasive high-grade human tumors such as glioblastoma multiforme (U251), neuroblastoma (SK-N-AS), breast cancer (MDA-MB-231), prostate cancer (PC-3), and non-small cell lung cancer (CRL-5904). The cell lines expressing low levels of uPAR were derived from tumors of the colon (COLO-320)

breast (MCF-7), metastatic neuroblastoma (NB-1691), and SCLC (CRL-5824, CRL-5869, CCL-257). uPAR and uPA expression levels were confirmed by quantitative real-time PCR (RT-PCR) (FIG. 6B) and immunohistochemical analysis (FIG. 6C). Interestingly, uPAR was expressed both on the cell surface and in the cytoplasm of tumor cells, while nuclei lacked uPAR signal.

Example 7

Attraction of Stem Cells to Tumors Expressing uPAR

The role of the uPA/uPAR system in stem cell migration was investigated using the immortalized neural stem cell line (NSC) HB1.F3.C1 and bone marrow-derived mesenchymal stem cells (MSC) (passages 5-6) for in vitro cell migration assays. Five cancer cell lines expressing high levels of uPAR (SK-N-AS, U251, PC-3, MDA-MB-231, and CRL-5904) and five cancer cell lines expressing low levels of uPAR (COLO-320, NB-1691, CRL-5824, CRL-5869, and MCF-7) as determined in Example 6 were utilized for this experiment.

Figure 7:
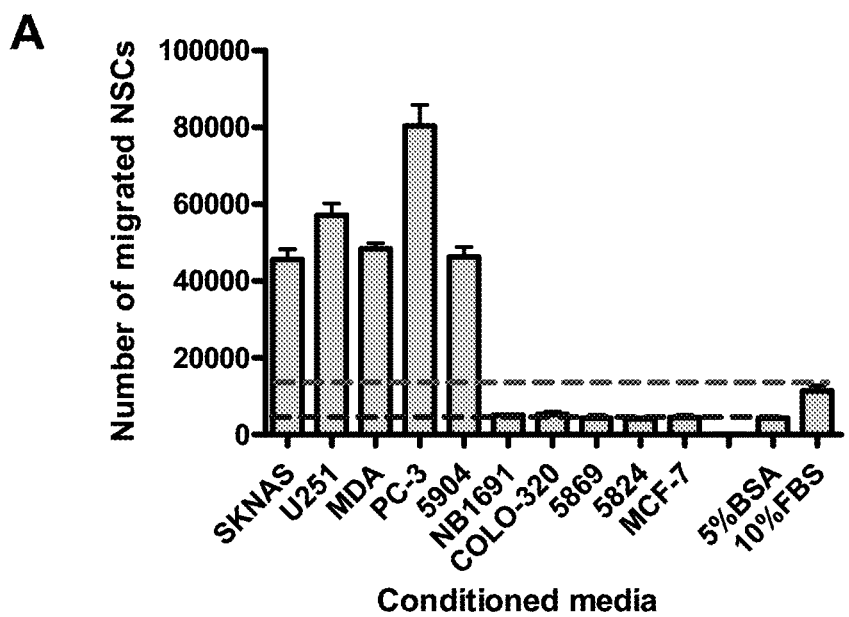
FIG. 7: Correlation of uPAR expression on cancer cell lines and attraction of stem cells. In vitro migration assays were performed using tumor-conditioned media and (A) immortalized neural stem cell line HB1.F3.C1 or (B) bone marrow-derived mesenchymal stem cells (passages 5-6).
Figure 7:
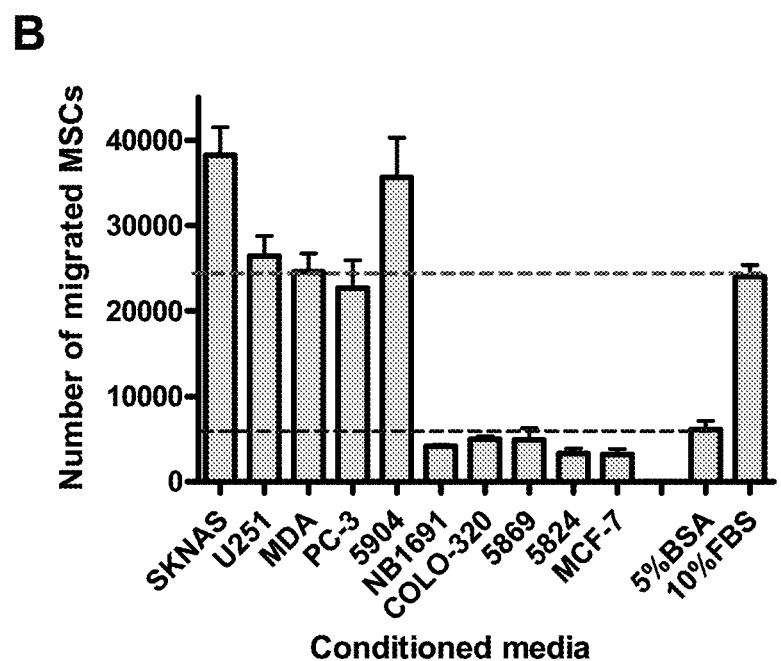

NSCs exhibited a robust migration to conditioned media derived from the tumor cells with high levels of uPAR expression, and a low level of migration to conditioned media from tumor cells with low levels of uPAR expression (FIG. 7A). A similar migration pattern was detected for the MSCs (FIG. 7B). Overall, NSCs showed a higher level of migration than MSCs (40-80% of cells migrated versus 20-40% of cells migrated). The strong observed correlation between uPAR expression and NSC and MSC migration indicates that activation of the uPA/uPAR system is responsible for recruitment of both neural and mesenchymal stem cells to tumors.

Figure 8:
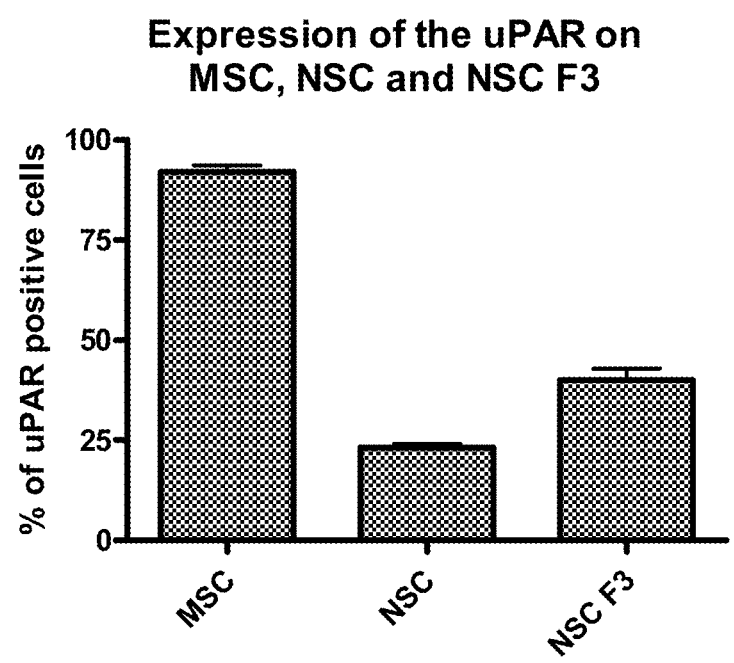
FIG. 8: Expression of uPAR on mesenchymal and neural stem cells.

Both stem cell lines utilized in this experiment were found to express high levels of uPAR receptor (FIG. 8).

Example 8

Detection of uPA and uPAR in Conditioned Media

Figure 9:
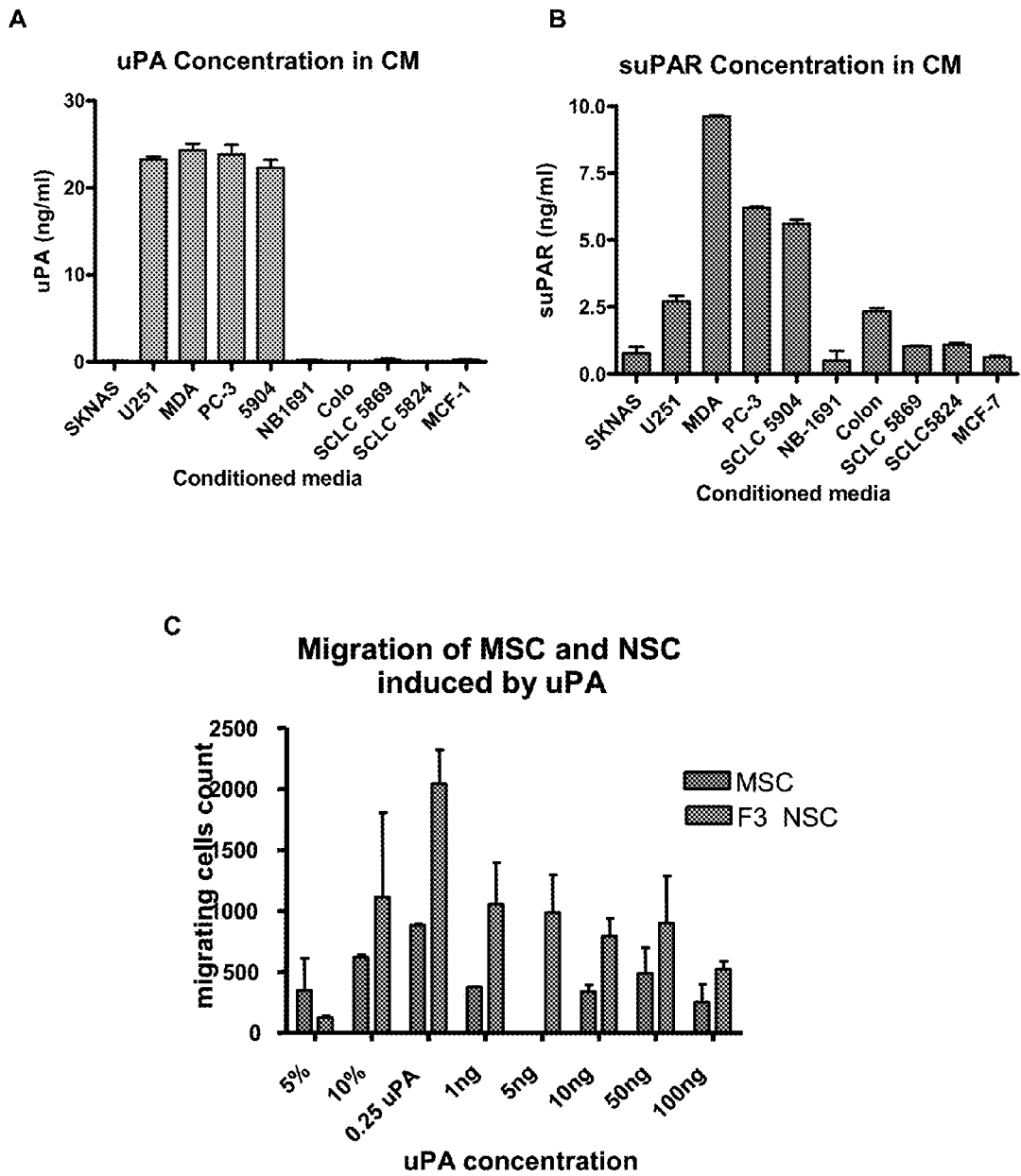
FIG. 9: (A) uPA concentration in tumor-conditioned media from various cancer cell lines was determined by ELISA. (B) suPAR concentration in tumor-conditioned media from various cancer cell lines was determined by ELISA. (C) Induction of MSC and NSC migration by uPA.

Cleavage of uPAR occurs at its GPI anchor by endogenous phospholipase D, leading to release of intact uPAR. Further cleavage of uPAR at its D1 or D2 domains generates soluble suPAR fragments. suPAR has been detected in sera of patients affected by different diseases, including various forms of cancer (Aref 2003; Werle 2004).

uPA and suPAR levels in conditioned media were measured by ELISA (FIGS. 9A and 9B). These results indicate that increased uPAR expression in tumor cells is associated with increased uPAR shedding and release of suPAR into the conditioned media (FIG. 9B), and high levels of the active form of uPA (FIG. 9A).

Example 9

Induction of Stem Cell Migration by uPA

To determine whether the increased stem cell migration observed in the presence of tumor cells expressing high levels of uPAR was induced by the activity of uPA or some other molecule, the ability of various concentrations of the recombinant active form of uPA to induce NSC and MSC migration was measured in serum-free media (DMEM, RPMI, F-K12). Moderate induction of stem cell migration was detected at 0.25 ng of recombinant uPA (FIG. 9C). Higher concentrations of uPA did not further increase stem cell migration.

Example 10

Inhibition of Stem Migration by uPAR Inhibitors

Figure 10:
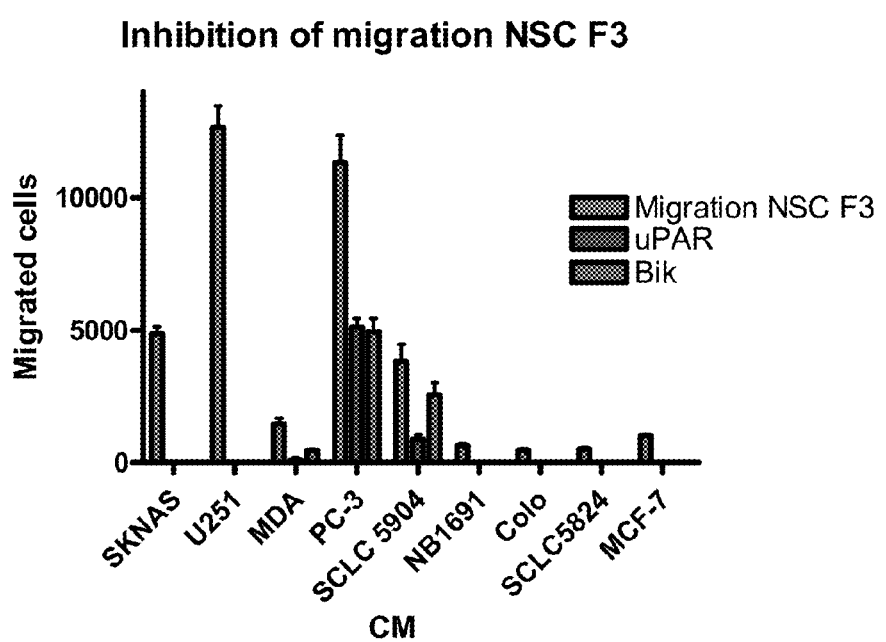
FIG. 10: Inhibition of NSC F3 stem cell migration by anti-uPAR antibodies and bikunin.

The effect of uPAR inhibitors on stem cell migration was examined in order to verify that increased stem cell migration to tumor cells expressing high levels of uPAR was dependent on uPAR. Bikunin, a physiological inhibitor of uPA, and various anti-uPAR antibodies were applied to the lower chamber of the migration assay system. Each of the inhibitors tested effectively inhibited stem cell migration (FIG. 10).

Example 10

Correlation of Cytokine Profile and Stem Cell Attraction

To identify other chemokines involved in stem cell tropism to tumor cells, cytokine arrays were used to screen conditioned media derived from tumor cells expressing high or low levels of uPAR. Cell lines utilized for this experiment were MDA-MD-231, MCF-7, CRL-5904, CRL-5824, U251 and PC-3 cells.

Figure 11:
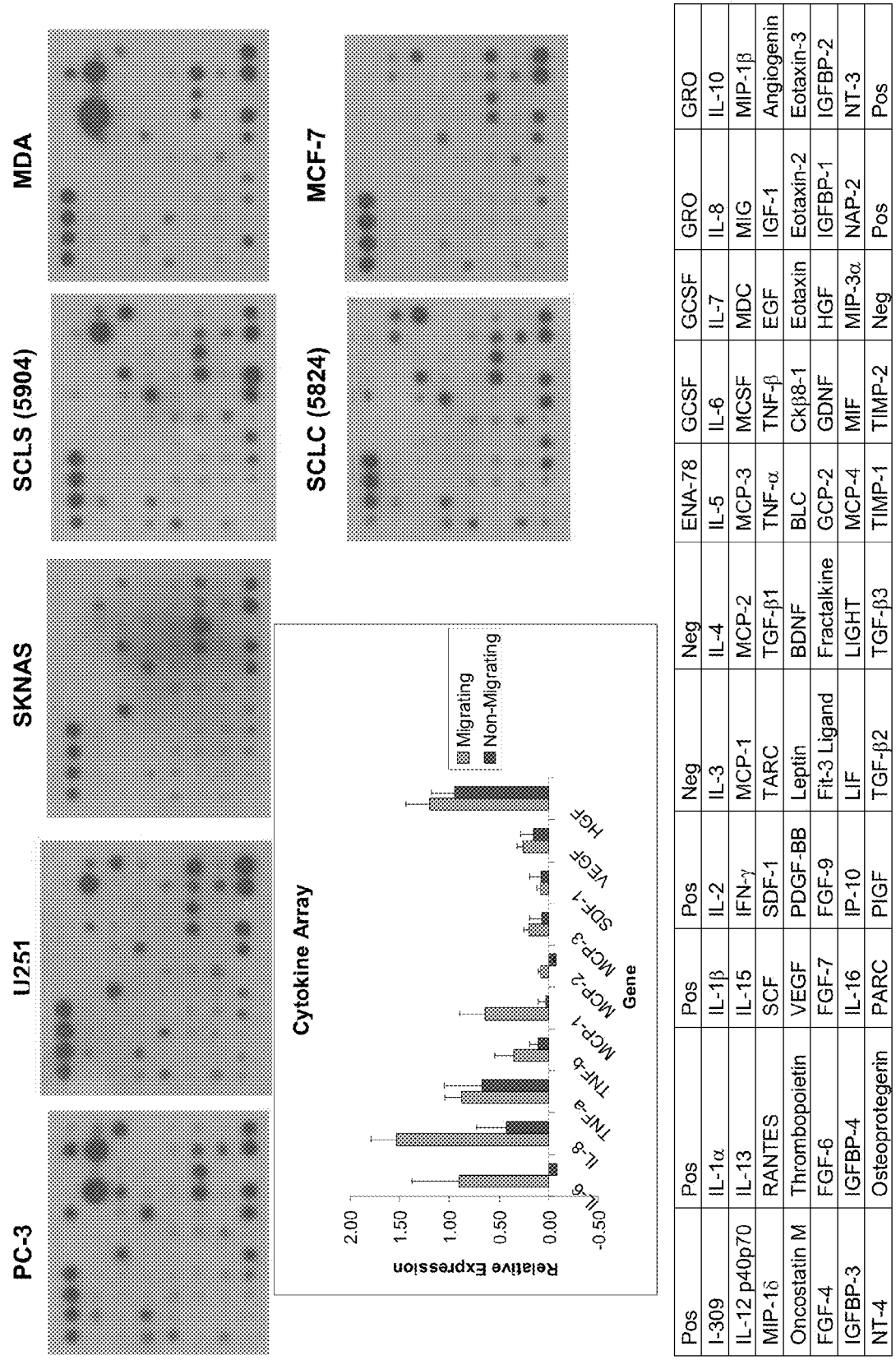
FIG. 11: Cytokine expression profiles in various cancer cell lines.

The results of this experiment are set forth in FIG. 11. CM from PC-3 cells exhibited induction of IL-6, IL-8, MCP-1 when compared to CM derived from CRL-5824 and MCF-7 cells. CM derived from U251 cells also showed induction of IL-8 and MCP-1, as well as HGF and VEGF. SK-N-AS cells displayed selective induction of MCP-1 and HGF. Comparative analysis of breast cancer cell lines showed significant induction of IL-6 and IL-8 in CM from MDA-MD-231 cells relative to CM from the low uPAR-expressing MCF-7 line. Comparison of lung CRL-5904 and CRL-5824 CM revealed significant differences in the expression of IL-8 and TIMP-2. Together, these results suggest that uPAR is a pleiotropic molecule involved in activation of the different signaling pathways involved in cell migration, extracellular proteolysis and cell survival. Of note, induction of the uPA/uPAR system on tumor cells is associated with activation of diverse signaling mechanisms that results in stem cell attraction.

Example 11

Effect of Normoxic Versus Hypoxic Conditions on Cancer Cell uPAR Expression

Figure 12A:
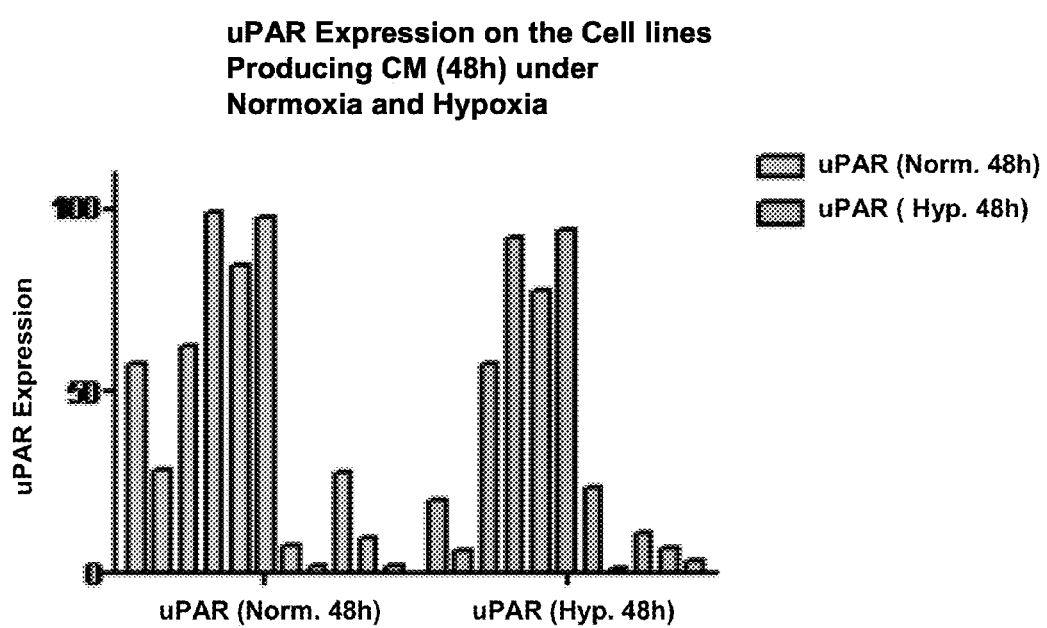
FIG. 12: (A) and (B) uPAR expression on tumor cells cultured under normoxic or hypoxic conditions. (C) In vitro migration assays revealed no significant change in stem cell migration toward conditioned media produced under normoxic or hypoxic conditions.
Figure 12B:
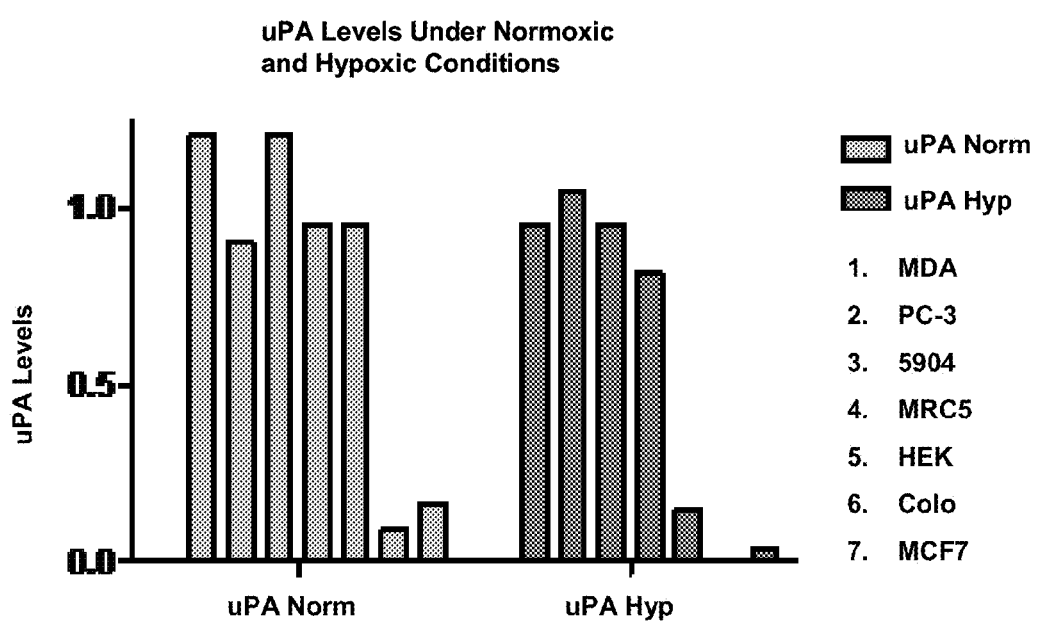
Figure 12C:
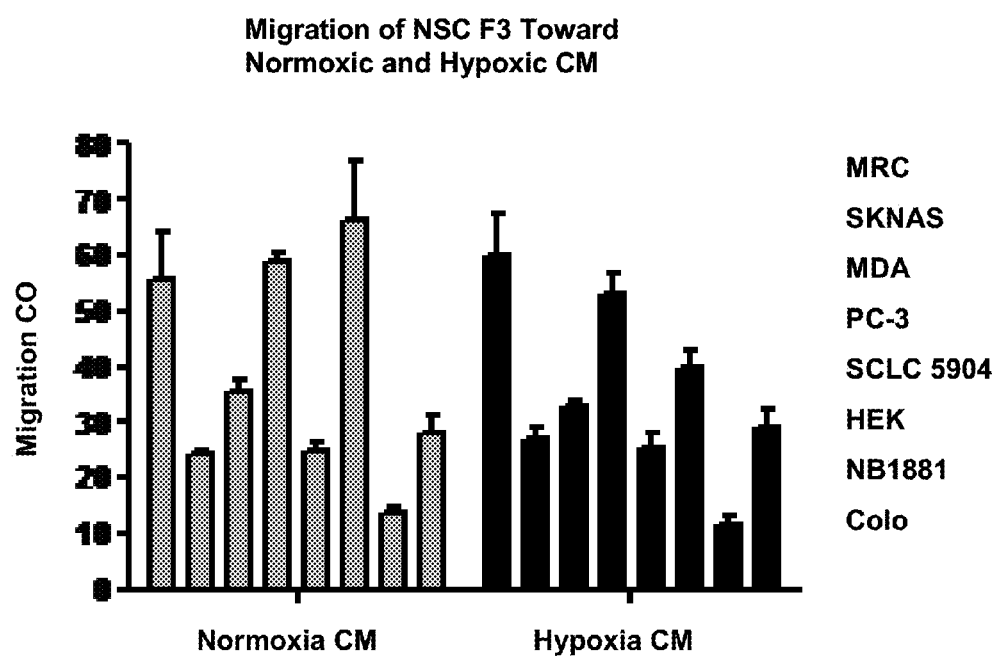

In order to elucidate the molecular mechanisms of stem cell migration to tumor cell-conditioned media, expression of uPAR on tumor cells that had been cultured for 48 hours under normoxic or hypoxic conditions to produce conditioned media was investigated. Cells cultured under normoxic or hypoxic conditions displayed similar levels of uPAR expression (FIG. 12). The levels of uPA ligand in the conditioned media of selected cell lines also remained unchanged after 48 hours of culture under normoxia or hypoxia (FIG. 12). In vitro migration assays revealed no significant change in stem cell migration toward conditioned media produced under normoxic or hypoxic conditions (FIG. 12). This indicates that migration depends on activation of the uPA/uPAR system independent of hypoxia. In vitro hypoxia does not induce migration of stem cells and does not change the status of uPA/uPAR system in the serum-free conditioned media.

Example 12

Tumorigenicity of SCLC Cell Lines In Vivo

To study SCLC progression in vivo, human fetal lung tissue was engrafted under the kidney capsule in SCID mice and allowed to grow for two months. After two months, unsorted CRL-5824, CRL-5904, or CRL-5869 cells transduced with GFP retrovirus were injected into the human lung tissue xenograft at doses of $1\times10^6$, $1\times10^5$, $1\times10^4$, or $1\times10^3$ cells (four mice per group). Eight to ten weeks after injections, mice were sacrificed and the human lung xenograft and mouse organs (lung, liver, kidney, spleen and brain) were collected and fixed in 4% paraformaldehyde/PBS overnight at 4° C. Tissues were incubated for 24 hours in 9% sucrose at 4° C., followed by 24 hours in 30% sucrose, after which tissues were embedded in OCT and frozen cryostat sections (10 μm) were prepared. Tissues were stained with hematoxylin and eosin (H&E) for routine histological analysis. Sections were immunostained with uPAR antibodies (American Diagnostica, 3936) for detection of uPAR-positive cells in primary and secondary tumor mass. Briefly, after quenching of endogenous peroxidases (0.3% hydrogen peroxide/PBS, 30 minutes), sections were rinsed in PBS and blocked with Serum-free Protein Block (DakoCytomation, X0909) for one hour at room temperature, followed by incubation with uPAR primary antibody (10 μg/ml, diluted in Antibody Diluent, DakoCytomation, S0809) for 16 hours at 4° C. After rinses, sections were incubated for one hour with biotinylated anti-mouse IgG secondary antibody (2 μg/ml; Vector, BA-2001) in Antibody Diluent. Immunoreactivity was detected using a Vectastain ABC Elite kit (Vector, PK-6100) and Peroxidase substrate kit (Vector, SK-4100), followed by light counterstaining of cell nuclei with hematoxylin. Tissues were dehydrated in graded ethanol and xylenes, and mounted with Cytoseal 60 (Richard-Allan Scientific, 8310-16). Low- and high-magnification images were obtained using a Nikon Eclipse TE2000-U microscope (Nikon Instruments) equipped with brightfield and fluorescence illumination, SPOT RT Slider digital camera (Diagnostic Instruments) and UV-2A B-2E/C (GFP) epi-fluorescence filter. Images were processed using SPOT Advanced and Adobe Photoshop software.

All three SCLC cell lines tested showed high tumorigenic potential and formed tumors within 8-10 weeks in the human fetal lung xenograft. The unsorted bone marrow (CRL-5824) cells gave rise to tumors in mice when $1\times10^6$ or $1\times10^5$ cells were injected, whereas injection of $1\times10^4$ cells led to tumors in only two out of four animals. Injection of $1\times10^3$ unsorted lung, bone marrow, and brain cells showed no tumorigenicity.

Example 13

Tumorigenic and Metastatic Potential of uPAR-Positive SCLC Cells In Vivo

Figure 13:
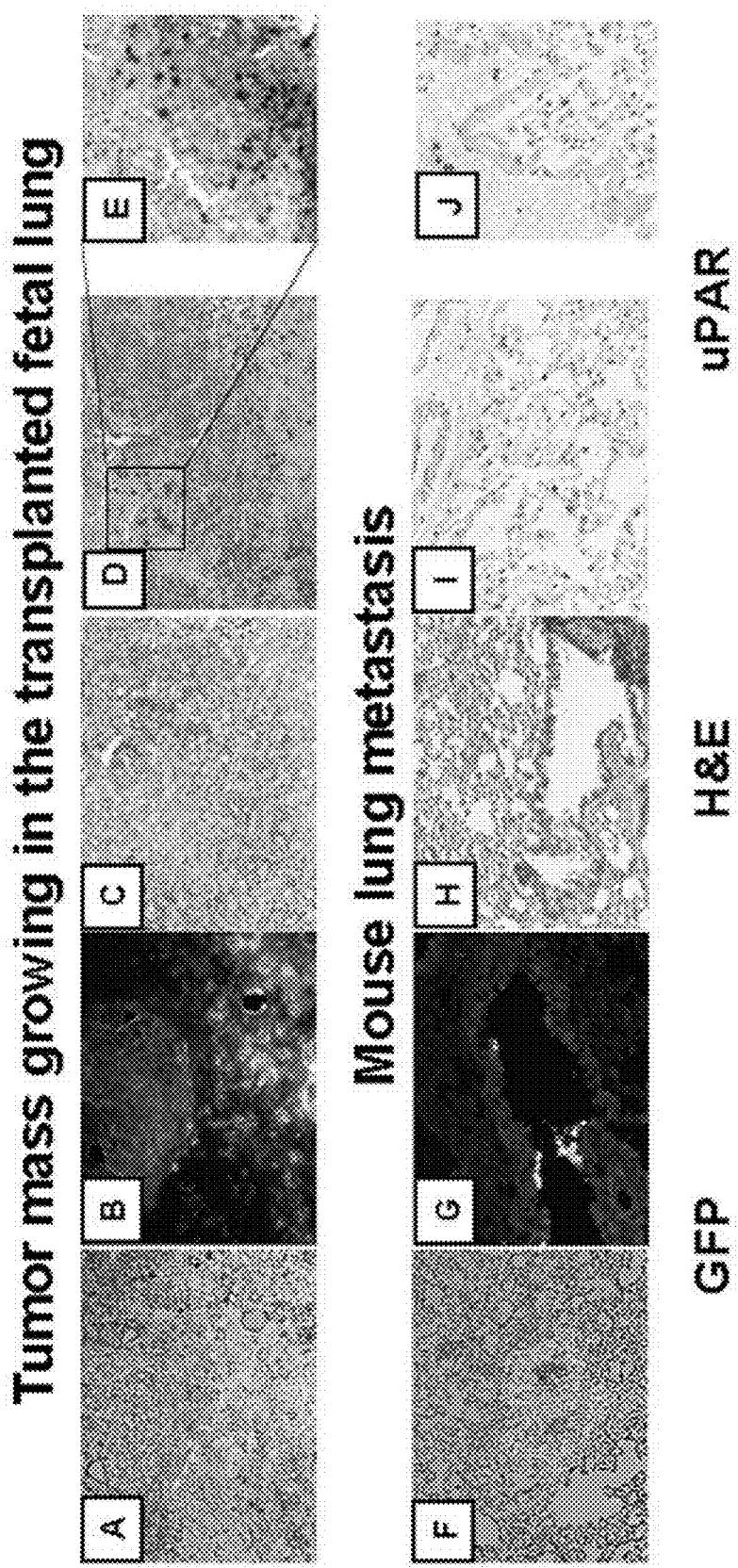
FIG. 13: Invasion of bone marrow-derived cell lines (CRL-5824) in SCID mice. (A)-(E) Tumor mass growing in situ in the transplanted human fetal lung. Green fluorescent protein (GFP) fluorescence (A, B), H&E (C), uPAR immunohistochemstry (D, E). (F)-(J) Metastasis in the mouse lung. GFP fluorescence (F, G), H&E (H), uPAR immunohistochemstry (I, J). Magnification 10× (A-D; F-I) and 20× (E, J).
Figure 14:
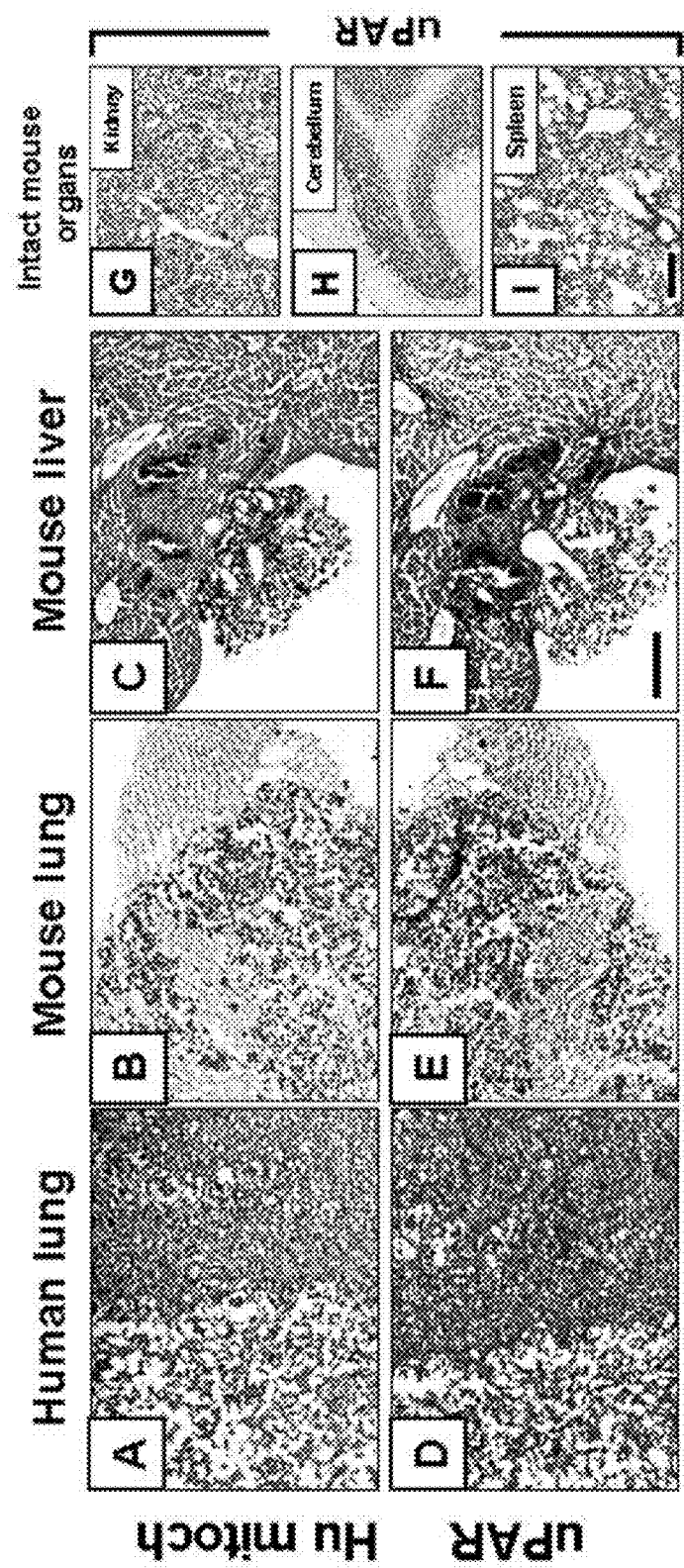
FIG. 14: Invasion of brain-derived cell lines (CRL-5904) in SCID mice. Tumor mass growing in situ in the transplanted human fetal lung (A, D). Metastasis in the mouse lung (B, E) and liver (C, F). Immunohistochemical staining for human mitochondria (A-C) and uPAR (D-F). Intact mouse organs stained for human mitochondria (G-I). Scale bars, 200 μm (A-I).

To investigate the tumorigenic potential of uPAR-positive cells, the experiment set forth in Example 12 was repeated using GFP-expressing sorted uPAR-positive cells, which represented ~1% of the bone marrow cell line (CRL-5824, 1000 cells total). After two months, uPAR-positive cells generated tumors in human lung xenografts in three out of four animals when injected at doses as low as $1\times10^3$ cells. Importantly, in addition to primary tumor growth, injection of the human SCLC cell lines also formed distant metastases in the host mouse lung and liver as detected by GFP fluorescence (FIGS. 13F and 13G) and anti-human mitochondria antibodies (FIGS. 13B and 14C), whereas malignant cells were not observed in the kidney, spleen and brain of the host mouse (FIGS. 14G, 14H, and 14I). Immunohistochemical analysis of fetal lung xenografts revealed the presence of uPAR-positive tumor cells (FIG. 13A-13E; FIGS. 14A and 14D). uPAR-positive cells were also detected in the host mouse lung and liver, suggesting that cells with high uPAR expression levels are capable of metastasizing to distant organs (FIG. 13F-13J; FIGS. 14B, 14C, 14E, and 14F). It was confirmed that uPAR-positive cell metastases were derived from the injected human SCLC cell lines (CRL-5904) by staining with anti-human mitochondria antibody, which was positive in the primary tumor bed (FIG. 14A), as well as in the metastatic tumor sites in host mouse lung and liver (FIGS. 14B and 14C).

Example 14

Characterization of Migrating Cancer Stem Cells

In vitro comparative analysis is performed on a panel of normal human stem cells (neural, mesenchymal, mesodermal) and our proposed "migrating cancer stem cells" derived from established tumor cell lines (brain U251, breast MDA, lung 5904) and primary tumor specimens (glioblastoma, breast carcinoma, lung carcinoma). The cell surface expression of CD87 is determined by FACS analysis and the level of CD87 mRNA measured by RT-PCR. CD87(+) and CD87(−) cell populations are isolated from each type of normal stem cell and tumor. The CD87(+) cells from primary tumor specimens are further sorted by colony forming assay and clonal chromosome analysis to distinguish cancer stem cells from normal stem cells present in the tumor specimen.

Specific characteristics of the CD87(+) and CD87(−) normal and cancer derived stem cells that are evaluated include:
a) uPAR/uPA system activation and expression using migration and invasion: Boyden chamber assays, Proliferation and Apoptotic assays;
b) Level of telomerase activity with TRAPEZE® ELISA Telomerase Detection System;
c) Level of p53 suppressor protein as determined by ELISA, Western blot analysis and Immunocytochemistry.

During tumor progression, cells that are responsible for tumor maintenance and metastasis possess several stem cell-like properties including self-renewal, evasion of apoptosis, unlimited potential for replication, ability to remodel tissue during invasion, and migration to distant sites. uPA and uPAR have the ability to support such a malignant phenotype through several mechanisms such as matrix degradation, stimulation of cell mobility through the control of cytoskeleton and focal adhesion, stimulation of cell proliferation and protection from apoptosis (Alfano 2005).

The p53 tumor suppressor gene regulates cell cycle progression in normal cells. The p53 protein serves as a checkpoint, which can become upregulated in response to a variety of stress stimuli such as ionizing radiation, chemotherapeutic agents, oxidative stress and hypoxia (Giacci 1998). Upon activation, p53 protein transcriptionally activates genes responsible for cell cycle arrest, apoptosis and DNA repair. Mutated forms of the p53 gene are involved in development of 50% of all human tumors (Benini 1998). Riccio et al. demonstrated that wild-type p53 is a negative regulator of uPA expression, whereas mutated p53 stimulates uPA promoter activity (Riccio 1985). A recent study by Shetty et al suggests that uPA at low concentrations (10-100 ng/ml) induces increased p53 protein levels, thus resulting in a moderate degree of apoptosis in lung epithelial cells (Shetty 2005). This may be considered as a normal physiological response of p53 protein to low levels of uPA. However, high concentrations of uPA (100-1000 ng/ml) lead to decreased p53 protein levels, with gradual reduction in apoptosis. uPA-induced p53 expression does not involve increased p53 mRNA. However, uPA can stabilize the level of expressed oncoprotein, Mdm2, a suppressor of p53 protein. An increase in p53 levels leads to downregulation of uPA expression. Thus, uPA and p53 proteins are part of a negative regulatory feedback loop. Oncogenic mutations of p53 protein can activate the uPA/CD87 pathway, which may in turn render the cells resistant to apoptosis. In this example, the correlation between p53 gene expression (mutated or wild type) and activation of the uPA/CD87 system in "migrating cancer stem cells" derived from various human cancers, including brain, breast and lung cancer is investigated.

Another feature of normal stem cells is high telomerase activity. Telomerase is a reverse transcriptase that prevents shortening of telomeres, a major determinant of regulation of cell survival. Activation of telomerase is required for self-renewal and proliferative expansion of stem cells, activated lymphocytes and cancerous cells (Blasco 2005). In contrast to germ cells, most somatic cells and adult stem cells do not express sufficient telomerase to maintain telomere length indefinitely. The progressive process of telomere loss (associated with aging, cancer or premature ageing syndromes) eventually leads to critically short telomeres, which triggers a DNA damage response that results in cell arrest and apoptosis. This effect coincides with upregulation of p53 tumor-suppressor gene (d'Adda di Fagagna 2003; Takai 2003).

The level of telomerase activity in CD87(+) and CD87(−) cells correlates with cancer stem cellness as reflected in the correlation of telomerase activity with CD87 and p53 expression. Stem cells expressing high telomerase activity have longer lifespan, but no tumorigenic activity. The CD87 positive/low p53 and telomerase-positive cells derived from malignant human tumors, on the other hand, display high tumorigenic potential, representing migrating cancer stem cells.

The ability of uPAR (CD87) over-expression to confer tumorigenic potential in vivo is shown by assessing the tumorigenic potential of the CD87(+) and CD87(−) "migrating cancer stem cell" populations derived from the primary tumor specimens as described above. This is determined by orthotopic injection of specified numbers of cells into adult female NOD/SCID mice, followed by observation over time for tumor formation (monitored by in vivo Xenogen imaging). Orthotopic implantation of CD87(+) and CD87(−) cells derived from the following primary tumors specimens are grown as follows:

a) Glioma—intracranial;

b) Breast carcinoma—intramammary fat pad;

c) Lung carcinoma—intrapulmonary (lung pleural space).

d) Re-isolated CD87 cells from formed tumors that are serially passaged through additional animals are evaluated for retention of tumorigenic potential.

Overexpression of CD87 confers tumorigenic potential in the in vivo system as is further characterized and supported by chromosomal mapping and transcriptional profiling.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

TABLE 1

FACS analysis of primary and metastatic phenotypes

|   | Antibodies | CRL-5869 (lung) | CCL-257 (lung) | CRL-5824 (BM) | CRL-5903 (BM) | CRL-5904 (brain) | CRL-5828 (brain) |
|---|---|---|---|---|---|---|---|
| 1* | CD13 PE | 1.4 | 1.9 | 2.6 | 77.2 | 33.0 | 28.3 |
| 2* | CD29 PE | 20.7 | 98.3 | 25.1 | 92.0 | 99.2 | 89.7 |
| 3** | CD34 FITC | 2.1 | 0.7 | 0.4 | 0.8 | 0.8 | 1.6 |
| 4* | CD44 FITC | 7.7 | 1.1 | 39.3 | 87.7 | 98.7 | 96.5 |
| 5* | CD87 FITC | 3.2 | 2.1 | 1.2 | 3.8 | 1.1 | 2.5 |
| 6** | CD90 PE | 2.1 | 2.4 | 2.7 | 5.0 | 0.7 | 1.4 |
| 7** | CD105 PE | 2.6 | 3.5 | 3.2 | 8.3 | 34.3 | 18.4 |
| 8* | CD109 PE | 0.9 | 0.4 | 0.1 | 4.0 | 1.2 | 3.2 |
| 9* | CD166 FITC | 84.4 | 89.6 | 98.0 | 76.7 | 96.9 | 94.3 |
| 10** | CD133 PE | 1.8 | 79.7 | 10.2 | 8.7 | 0.9 | 1.7 |
| 11** | ABCG2 FITC | 1.8 | 1.3 | 0.4 | 0.7 | 1.2 | 1.0 |
| 12* | CXCR4 FITC | 0.3 | 0.5 | 0.6 | 0.8 | 0.6 | 0.6 |

*Tumor cell surface determinants;
**stem cell determinants

REFERENCES

1. Aguirre Ghiso, J. A., et al. 1999. Deregulation of the signaling pathways controlling urokinase production. Its relationship with the invasive phenotype. Eur J Biochem 263 (2):295-304.
2. Alfano, D., et al. 2005. The urokinase plasminogen activator and its receptor: role in cell growth and apoptosis. Thromb Haemost 93(2):205-211.
3. Alfano, D., Iaccarino, I., Stoppelli, M. P. 2006. Urokinase signaling through its receptor protects against anoikis by increasing BCL-xL expression levels. J Biol Chem 281: 17758-17767.
4. Al-Hajj, M., et al. 2003. Prospective identification of tumorigenic breast cancer cells. Proc Natl Acad Sci USA 100 (7):3983-3988.
5. Almasi, C. E., et al. 2005. Prognostic impact of liberated domain I of the urokinase plasminogen activator receptor in squamous cell lung cancer tissue. Lung Cancer 48(3): 349-355.
6. Aref, S., et al. 2003. Urokinase plasminogen activator receptor and soluble matrix metalloproteinase-9 in acute myeloid leukemia patients: a possible relation to disease invasion. Hematology 8(6):385-391.
7. Benini, E., et al. 1998. p53 expression in human carcinomas: could flow cytometry be an alternative to immunohistochemistry? J Histochem Cytochem 46(1)41-48.
8. Bjerkvig, R., et al. 2005. Opinion: the origin of the cancer stem cell: current controversies and new insights. Nat Rev Cancer 5(11):899-904.
9. Blasco, M. A. 2005. Telomeres and human disease: ageing, cancer and beyond. Nat Rev Genet 6(8):611-622.
10. Blasi, F. and P. Carmeliet. 2002. uPAR: a versatile signaling orchestrator. Nat Rev Mol Cell Biol 3(12):932-943.
11. Brabletz, T., et al. 2005a. Opinion: migrating cancer stem cells—an integrated concept of malignant tumour progression. Nat Rev Cancer 5(9):744-749.
12. Brabletz, T., et al. 2005b. Invasion and metastasis in colorectal cancer: epithelial-mesenchymal transition, mesenchymal-epithelial transition, stem cells and beta-catenin. Cells Tissues Organs 179(1-2):56-65.
13. Brat, D. J., Bellail, A. C., Van Meir, E. G. 2005. The role of interleukin-8 and its receptors in gliomagenesis and tumoral angiogenesis. Neuro-oncol 7:122-133.

14. Czekay, R. P., et al. 2001. Direct binding of occupied urokinase receptor (uPAR) to LDL receptor-related protein is required for endocytosis of uPAR and regulation of cell surface urokinase activity. Mol Biol Cell 12(5):1467-1479.
15. d'Adda di Fagagna, F., et al. 2003. A DNA damage checkpoint response in telomere-initiated senescence. Nature 426(6963):194-198.
16. Dean, M., Foto, T., Bates, S. 2005. Tumour stem cells and drug resistance. Nat Rev Cancer 5:275-284.
17. D'Alessio, S., et al. 2004. Antisense oligodeoxynucleotides for urokinase-plasminogen activator receptor have anti-invasive and anti-proliferative effects in vitro and inhibit spontaneous metastases of human melanoma in mice. Int J Cancer 110(1):125-133.
18. Dick, J. E. 2003. Breast cancer stem cells revealed. Proc Natl Acad Sci USA 100(7):3547-3549.
19. Foekens, J. A., et al. 2000. The urokinase system of plasminogen activation and prognosis in 2780 breast cancer patients. Cancer Res 60(3):636-643.
20. Galli, R., et al. 2004. Isolation and characterization of tumorigenic, stem-like neural precursors from human glioblastoma. Cancer Res 64(19):7011-7021.
21. Gao, C. F., et al. 2005. Proliferation and invasion: plasticity in tumor cells. Proc Natl Acad Sci USA 102(30): 10528-10533.
22. Giacci, A. J., Kastan, M. B. 1998. The complexity of p53 modulation: emerging patterns from divergent signals. Genes Dev 12(19):2973-2983.
23. Hope, K. J., Jin, L., Dick, J. E. 2004. Acute myeloid leukemia originates from a hierarchy of leukemic stem cell classes that differ in self-renewal capacity. Nat Immunol 5(7):738-743.
24. Kamikura, D. M., et al. 2000. Enhanced transformation by a plasma membrane-associated met oncoprotein: activation of a phosphoinositide 3'-kinase-dependent autocrine loop involving hyaluronic acid and CD44. Mol Cell Biol 20:3482-3496.
25. Kim, C. F., et al. 2005. Identification of bronchioalveolar stem cells in normal lung and lung cancer. Cell 121:823-835.
26. Kobayashi, H., et al. 2002. CD44 stimulation by fragmented hyaluronic acid induces upregulation of urokinase-type plasminogen activator and its receptor and subsequently facilitates invasion of human chondrosarcoma cells. Int J Cancer 102:379-389.
27. Kondo, T., Setoguchi, T., Taga, T. 2004. Persistence of a small subpopulation of cancer stem-like cells in the C6 glioma cell line. Proc Natl Acad Sci USA 101(3):781-786.
28. Lahad, J. P., Mills, G. B., Coombes, K. R. 2005. Stem cell-ness: a "magic marker" for cancer. J Clin Invest 115 (6):1463-1467.
29. Lakka, S. S., et al. 2001. Regulation of the uPA gene in various grades of human glioma cells. Int J Oncol 18(1): 71-79.
30. Lakka, S. S., et al. 2005. Specific interference of urokinase-type plasminogen activator receptor and matrix metalloproteinase-9 gene expression induced by double-stranded RNA results in decreased invasion, tumor growth, and angiogenesis in gliomas. J Biol Chem 280(23)21882-21892.
31. Lee, D. H., et al. 2003. Macrophage inhibitory cytokine-1 induces the invasiveness of gastric cancer cells by up-regulating the urokinase-type plasminogen activator system. Cancer Res 63(15):4648-4655.
32. Levy, L., et al. 2002. Transcriptional activation of inter-leukin-8 by beta-catenin-Tcf4. J Biol Chem 277:42386-42393.
33. Li, A., et al. 2003. IL-8 directly enhanced endothelial cell survival, proliferation, and matrix metalloproteinase production and regulated angiogenesis. J Immunol 170:3369-3376.
34. Margheri, F., et al. 2005. Effects of blocking urokinase receptor signaling by antisense oligonucleotides in a mouse model of experimental prostate cancer bone metastases. Gene Ther 12(8)702-714.
35. Meijer-van Gelder, M. E., et al. 2004. Urokinase-type plasminogen activator system in breast cancer: association with tamoxifen therapy in recurrent disease. Cancer Res 64(13):4563-4568.
36. Miletti-Gonzalez, K. E., et al. 2005. The CD44 receptors interacts with P-glycoprotein to promote cell migration and invasion in cancer. Cancer Res 65:6660-6667.
37. Montuori, N., et al. 2005. Soluble and cleaved forms of the urokinase-receptor: degradation products or active molecules? Thromb Haemost 93(2):192-198.
38. Patrawala, L., et al. 2006. Highly purified CD44+ prostate cancer cells from xenograft human tumors are enriched in tumorigenic and metastatic progenitor cells. Oncogene 25:1696-1708.
39. Pisick, E., Jagadeesh, S., Salgia, R. 2003. Small cell lung cancer: from molecular biology to novel therapeutics. J Exp Ther Oncol 3(6)305-318.
40. Pulukuri, S. M., et al. 2005. RNA interference-directed knockdown of urokinase plasminogen activator and urokinase plasminogen activator receptor inhibits prostate cancer cell invasion, survival and tumorigenicity in vivo. J Biol Chem 280(43):36529-36540.
41. Rao, J. S., et al. 2005. Inhibition of invasion, angiogenesis, tumor growth, and metastasis by adenovirus-mediated transfer of antisense uPAR and MMP-9 in non-small cell lung cancer cells. Mol Cancer Ther 4(9):1399-1408.
42. Riccio, A., et al. 1985. The human urokinase-plasminogen activator gene and its promoter. Nucleic Acids Res 13(8):2759-2771.
43. Rigolin, G. M., et al. 2003. Soluble urokinase-type plasminogen activator receptor (suPAR) as an independent factor predicting worse prognosis and extra-bone marrow involvement in multiple myeloma patients. Br J Haematol 120(6):953-959.
44. Ross, J. A. 2004. Genetics and childhood cancer. Commentary on: inherited cancer in children: practical/ethical problems and challenges. Eur J Cancer 40(16):2471-2472.
45. Selleri, C., et al. 2005. Involvement of the urokinase-type plasminogen activator receptor in hematopoietic stem cell mobilization. Blood 105(5):2198-2205.
46. Shetty, S., Gyetko, M. R., Mazar, A. P. 2005. Induction of p53 by urokinase in lung epithelial cells. J Biol Chem 280(30):28133-28141.
47. Singh, S. K., et al. 2004. Identification of human brain tumour initiating cells. Nature 432(7015):396-401.
48. Takai, H., Smogorzewska, A., de Lange, T. 2003. DNA damage foci at dysfunctional telomeres. Curr Biol 13(17): 1549-1556.
49. Watters, J. W. and McLeod, H. L. 2003. Using genome-wide mapping in the mouse to identify genes that influence drug response. Trends Pharmacol Sci 24(2):55-58.
50. Werle, B., et al. 2004. Cathepsin B, plasminogenactivator-inhibitor (PAI-1) and plasminogenactivator-receptor (uPAR) are prognostic factors for patients with non-small cell lung cancer. Anticancer Res 24(6):4147-4161.
51. Zhou, S., et al. 2004. The ABC transporter Bcrp1/ABCG2 is expressed in a wide variety of stem cells and is a molecular determinant of the side-population phenotype. Nat Med 7:1028-1034.

52. Zoltan-Jones, A., et al. 2003. Elevated hyaluronan production induces mesenchymal and transformed properties in epithelial cells. J Biol Chem 278:45801-45810.

What is claimed is:

1. An in vitro small cell lung cancer (SCLC) cell population comprising more than 5% uPAR positive cancer stem cells, wherein the uPAR positive cancer stem cells are additionally selected from the group consisting of CD44 positive cancer stem cells, MDR positive cancer stem cells, tumorigenic cancer stem cells, and metastatic cancer stem cells.

2. The cancer cell population of claim 1 wherein the uPAR positive cancer stem cells have an increased chemoresistance to one or more chemotherapeutic agents versus uPAR negative SCLC cells.

3. The cancer cell population of claim 2 wherein the chemotherapeutic agent is cisplatin, etoposide, 5-FU or a combination thereof.

* * * * *